(12) United States Patent
Rabbani et al.

(10) Patent No.: US 9,777,312 B2
(45) Date of Patent: *Oct. 3, 2017

(54) DUAL POLARITY ANALYSIS OF NUCLEIC ACIDS

(75) Inventors: Elazar Rabbani, New York, NY (US); James J. Donegan, Long Beach, NY (US)

(73) Assignee: Enzo Life Sciences, Inc., New York, NY (US)

( * ) Notice: Subject to any disclaimer, the term of this patent is extended or adjusted under 35 U.S.C. 154(b) by 331 days.

This patent is subject to a terminal disclaimer.

(21) Appl. No.: 11/444,151

(22) Filed: May 31, 2006

(65) Prior Publication Data

US 2007/0281863 A1    Dec. 6, 2007
US 2012/0108443 A9    May 3, 2012

Related U.S. Application Data

(63) Continuation-in-part of application No. 10/096,076, filed on Mar. 12, 2002, which is a continuation-in-part of application No. 10/693,481, filed on Oct. 24, 2003, now abandoned, which is a continuation-in-part of application No. 09/896,897, filed on Jun. 30, 2001, now abandoned.

(51) Int. Cl.
C12Q 1/68    (2006.01)

(52) U.S. Cl.
CPC ......... *C12Q 1/6809* (2013.01); *C12Q 1/6813* (2013.01); *C12Q 1/6844* (2013.01)

(58) Field of Classification Search
None
See application file for complete search history.

(56) References Cited

U.S. PATENT DOCUMENTS

| | | |
|---|---|---|
| 4,563,417 A | 1/1986 | Albarella et al. |
| 4,724,202 A | 2/1988 | Dattagupta et al. |
| 4,732,847 A | 3/1988 | Stuart et al. |
| 4,868,104 A | 9/1989 | Kurn et al. |
| 4,994,373 A | 2/1991 | Stavrianopoulos et al. |
| 5,143,854 A | 9/1992 | Pirrung et al. |
| 5,227,292 A | 7/1993 | White et al. |
| 5,270,184 A | 12/1993 | Walker |
| 5,399,491 A | 3/1995 | Kacian et al. |
| 5,409,818 A | 4/1995 | Davey et al. |
| 5,432,065 A | 7/1995 | Fuller |
| 5,491,063 A | 2/1996 | Fisher et al. |
| 5,523,217 A | 6/1996 | Lupski |
| 5,545,540 A | 8/1996 | Mian |
| 5,605,662 A | 2/1997 | Heller et al. |
| 5,616,478 A | 4/1997 | Chetverin et al. |
| 5,641,658 A | 6/1997 | Adams et al. |
| 5,695,926 A | 12/1997 | Cros et al. |
| 5,716,785 A | 2/1998 | Van Gelder |
| 5,744,311 A | 4/1998 | Fraiser et al. |
| 5,824,517 A | 10/1998 | Cleuziat et al. |
| 5,849,480 A | 12/1998 | Cros et al. |
| 5,849,546 A | 12/1998 | Sousa et al. |
| 5,853,993 A | 12/1998 | Dellinger et al. |
| 5,856,092 A | 1/1999 | Dale et al. |
| 5,891,636 A | 4/1999 | Van Gelder |
| 5,919,523 A | 7/1999 | Sundberg et al. |
| 5,932,451 A | 8/1999 | Wang et al. |
| 5,972,607 A | 10/1999 | Kondo |
| 5,985,549 A * | 11/1999 | Singer et al. .............. 435/6.14 |
| 5,994,056 A | 11/1999 | Higuchi |
| 6,017,738 A | 1/2000 | Morris et al. |
| 6,040,138 A * | 3/2000 | Lockhart ............. C12Q 1/6809 435/6.11 |
| 6,103,474 A | 8/2000 | Dellinger et al. |
| 6,114,152 A | 9/2000 | Serafini et al. |
| 6,197,554 B1 | 3/2001 | Lin |
| 6,204,326 B1 | 3/2001 | Cook et al. |
| 6,214,553 B1 | 4/2001 | Szostak et al. |
| 6,238,868 B1 | 5/2001 | Carrino et al. |
| 6,241,060 B1 | 6/2001 | Gonzalez et al. |
| 6,242,189 B1 | 6/2001 | Kustu et al. |
| 6,251,601 B1 * | 6/2001 | Bao .................... C12Q 1/6837 422/400 |
| 6,251,639 B1 | 6/2001 | Kurn |

(Continued)

FOREIGN PATENT DOCUMENTS

| | | |
|---|---|---|
| CA | 2374436 | 11/2000 |
| EP | 0 231 495 | 12/1986 |

(Continued)

OTHER PUBLICATIONS

Forghani et al. (1991) J. of Clin. Microbiol. vol. 29 Bo 3. pp. 583-591.*
Baugh, L.R., et al., Quantative Analysis of MNRA Amplification by In Vitro Transcription, Nucl. Acids Res. 29:E29 (2001).
Boule, J.B., et al., Terminal Deoxynucleotidyl Transferase Indiscriminately Incorporates . . . J. Biol. Chem. 276:31388-31393 (2001).
Komura, J., et al., Terminal Transferase-Dependent PCR: A Versatile and Sensitive Method . . . Nucl Acids Res.26:1807-1811 (1998).
Krupp, G. et al., Unusual Promoter-Independent Transcription Reactionswith Bacteriophage . . . Nucl. Acids Res. 17:3023-3036 (1989).
McGiness, K.E. et al., Substitution of Ribonucleotides in the T7 RNA Polymerase . . . J. Biol. Chem. 277:2987-2991 (2002).

(Continued)

*Primary Examiner* — Prabha Chunduru
(74) *Attorney, Agent, or Firm* — Paul Diamond, Esq.

(57) ABSTRACT

This invention provides methods for characterizing the amounts of nucleic acids, including plus/minus determinations, the use of different constructs, the use of a library and a reference library. Expression may also be compared in two or more samples using the methods of this invention. Also provided are heterophasic arrays comprising labeled positive copies of nucleic acids hybridized to the array and labeled negative copies of nucleic acids hybridized to the array, in which the labeled positive copies are separately quantifiable from the labeled negative copies.

28 Claims, 2 Drawing Sheets

(56) References Cited

U.S. PATENT DOCUMENTS

| | | | |
|---|---|---|---|
| 6,261,782 B1 | 7/2001 | Lizardi et al. | |
| 6,268,147 B1 | 7/2001 | Beattie et al. | |
| 6,268,171 B1 | 7/2001 | Meyer et al. | |
| 6,277,579 B1 | 8/2001 | Lazar et al. | |
| 6,280,954 B1 | 8/2001 | Ulfendahl | |
| 6,326,489 B1 | 12/2001 | Church et al. | |
| 6,344,317 B2 | 2/2002 | Urnovitz | |
| 6,376,191 B1 | 4/2002 | Yu et al. | |
| 6,379,932 B1 | 4/2002 | Arnold et al. | |
| 6,423,552 B1 | 7/2002 | Lu et al. | |
| 6,451,588 B1 | 9/2002 | Egholm et al. | |
| 6,479,650 B1 | 11/2002 | Kool | |
| 6,485,944 B1 | 11/2002 | Church et al. | |
| 6,500,620 B2* | 12/2002 | Yu | C12Q 1/6809 435/6.11 |
| 6,531,300 B1 | 3/2003 | Haydock | |
| 6,537,747 B1 | 3/2003 | Mills, Jr. et al. | |
| 6,586,569 B1 | 7/2003 | Starzinski-Powitz et al. | |
| 6,696,256 B1 | 2/2004 | Li | |
| 6,730,517 B1 | 5/2004 | Koster et al. | |
| 6,858,412 B2 | 2/2005 | Willis et al. | |
| 7,064,197 B1 | 6/2006 | Rabbani et al. | |
| 9,163,280 B2 | 10/2015 | Rabbani | |
| 2002/0004204 A1 | 1/2002 | O'Keefe | |
| 2002/0110828 A1 | 8/2002 | Ferea et al. | |
| 2002/0168640 A1 | 11/2002 | Li et al. | |
| 2003/0044817 A1 | 3/2003 | Laird | |
| 2003/0050444 A1 | 3/2003 | Haydock | |
| 2003/0077609 A1 | 4/2003 | Jakobsen | |
| 2003/0082566 A1 | 5/2003 | Sylvan | |
| 2003/0104460 A1 | 6/2003 | Rabbani | |
| 2003/0118595 A1 | 6/2003 | Niemeyer et al. | |
| 2004/0110177 A1* | 6/2004 | Ullrich | C12Q 1/6883 435/6.16 |
| 2004/0161741 A1* | 8/2004 | Rabani et al. | 435/6 |
| 2004/0197779 A1 | 10/2004 | Apffel | |
| 2004/0209299 A1 | 10/2004 | Pinter et al. | |
| 2005/0100932 A1 | 5/2005 | Lapidus et al. | |
| 2005/0202455 A1 | 9/2005 | Rabbani et al. | |
| 2005/0233343 A1 | 10/2005 | Rabbani et al. | |
| 2005/0238658 A1* | 10/2005 | Maskell et al. | 424/200.1 |
| 2006/0014156 A1 | 1/2006 | Rabbani et al. | |
| 2006/0099601 A1 | 5/2006 | Rabbani et al. | |
| 2006/0257906 A1 | 11/2006 | Rabbani et al. | |
| 2007/0134707 A1 | 6/2007 | Gan | |

FOREIGN PATENT DOCUMENTS

| | | |
|---|---|---|
| EP | 0478319 | 4/1992 |
| EP | 0667393 | 8/1995 |
| EP | 0846776 | 6/1998 |
| EP | 1041160 | 10/2000 |
| EP | 1201768 | 5/2002 |
| WO | WO 92 08800 | 5/1992 |
| WO | WO 9208800 | 5/1992 |
| WO | WO95/24649 | 9/1995 |
| WO | WO96/06948 | 3/1996 |
| WO | WO 97 10365 | 3/1997 |
| WO | WO 98/45474 | 4/1998 |
| WO | WO 99/19510 | 4/1999 |
| WO | WO99/51773 | 10/1999 |
| WO | WO 99/58718 | 11/1999 |
| WO | WO99/58118 | 1/2000 |
| WO | WO 00/24936 | 5/2000 |
| WO | WO 00/26406 | 5/2000 |
| WO | WO 00/32823 | 6/2000 |
| WO | WO00/60116 | 10/2000 |
| WO | WO00/61806 | 10/2000 |
| WO | WO 0075356 | 12/2000 |
| WO | WO 01/05935 | 1/2001 |
| WO | WO01/13126 | 2/2001 |
| WO | WO 01/36681 | 5/2001 |
| WO | WO 01/40803 | 6/2001 |
| WO | WO00/61806 | 12/2001 |

OTHER PUBLICATIONS

Schenborn, E.T., et al., A Novel Transcription Property of SP6 and T7 RNA Polymerases . . . Nucl. Acids Res. 13:6223-6236 (1985).
Schmidt, W.M. et al., Controlled Ribonucleotide Tailing of CDNA Ends (CRTC) by Terminal . . . Nucl. Acids. Res. 24:1789-1791(1996).
Van Gelder, R.N. et al., Amplified RNA Synthesized From Limited Quantities Heterogenous CDNA, Proc. Natl. Acad Sci. USA 87:1663-1667 (1990).
Walker, G.T. et al., Isothermal In Vitro Amplification of DNA by a Restriction Enzyme . . . Proc. Natl. Acad. Sci. USA 89:392-396 (1992).
Adams., et al. Complementary DNA Sequencing: Expressed Sequence Tags . . . Science 252:1651-1656 (1991).
Afanassiev et al.,Preparation of DNA and Protein Micro Assays on Glass . . . Nucl. Acids Res. 28:E66 (2000).
Antopolsky, M. et al., Solid-Phase Synthesis of Peptide-Oligonucleotide . . . Helv. Chim Acta 82:2130-2140 (1999).
Arar, K., et al., Synthesis of Oligonucleotide-Peptide Conjugates . . . Tetrahedron Letter 34:8087-8090 (1993).
Arenkov, P., et al., Protein Microchips: Use for Immunoassay . . . Analytical Biochemistry 278:123-131 (2000).
Bazin, et al., Innovation and Perspectives in Solid Phase Synthesis . . . R. Epton, Mayflower Sci. Ltd. Birmingham, UK (1999).
Bergmann, F. et al., Solid Phase Synthesis of Directly Linked Peptide-Oligo . . . Tetrahedron Letters 36:1839-1842 (1995).
Brenner, S., et al., Encoded Combinatorial Chemistry, Proc. Natl. Acad. Sci. USA 89:5381-5383 (1992).
Cho, R.J., et al., A Genome-Wild Transcriptional Anaylsis . . . Mol. Cell 2:65-73 (1998).
De La Torre, B.G., et al., Stepwise Solid-Phase Synthesis . . . Tetrahedron Letters 35:2733-2736 (1994).
De La Torre, B.G., et al., Synthesis and Bonding Properties of Oligonucleotide-Peptide . . . Bioconjugate Chem. 10:1005-1012 (1999).
De Wildt, R.M., et al., Antibody Arrays for High-Output Screening . . . Nature Biotechnology 18:989-994 (2000).
Ede, N.J., et al., Routine Preparation of Thiol Oligonucleotides . . . Bioconjugate Chemistry 5:373-378 (1994).
Edwards, J.B.D.M., et al., Oligodeoxyribonucleotide Ligation . . . Nucl, Acids. Res. 19:5227-5232 (1991).
Endege, W.O., et al., Representative cDNA Libraries and Their Utility . . . Biotechniques 26:542-550 (1999).
Eritja, R., et al., Synthesis of Defined Peptide-Oligonucleotide Hybrids . . . Tetrahedron 47:4113-4120 (1991).
Gentalen, E. et al., A Novel Method for Determining Linkage Between DNA Sequences . . . , Nucl. Acid. Res.27:1485-1491 (1999).
Haab, B.B., et al.,Protein Microarrays for Highly Parallel Detection . . . Genome Biology 2:1-13 (2001).
Hirschhorn, J.N., et al., SBE-Tags: An Array-Based Method for Efficient . . . Proc. Natl. Acad. Sci. USA 97:12164-12169 (2000).
Kwoh, D.Y., et al., Transcription-Based Amplification System and Detection . . . Proc. Natl. Acad. Sci. USA 86:1173-1177 (1989).
Koonin, E.V., et al., The Phyology of RNA-Dependent RNA Polymerase . . . J. Gen. Virol. 72:2197-2206 (1991).
Lakobashvill, R., et al., Low Temperature Cycled PCR Protocol . . . Nucl. Acids. Res. 27:1566-1568 (1999).
Lockhart, D.J., et al., Expression Monitoring by Hybridization to High-Density . . . ,Nature Biotechnology14:1675-1680 (1996).
Lueking, A., et al., Protein Microarrays for Gene Expression . . . ,Anal. Biochem 270:103-111 (1999).
Matz, M., et al., Amplification of CDNA Ends Based on Template-Switching . . . ,Nucleic Acids Res. 27:1558-1560 (1999).
Mendoza, L.G., et al., High-Throughput Microarray-Based Enzyme-Linked . . . Biotechniques 27:778-788 (1999).
Needels, M.C., et al., Generation and Screening of an Oligonucelotide-Encoded . . . ,Proc. Natl. Acad.Sci. USA 90:10700-10704 (1993).
Okamoto, T., et al., Microarray Fabrication With Covalent Attachment of DNA . . . Nature Biotechnology 18:438-441 (2000).
Pastinen, T., et al., A System for Specific, High Throughput Genotyping . . . , Genome Research 10:1031-1042 (2000).

(56) References Cited

OTHER PUBLICATIONS

Pergolizzi, et al., U.S. Appl. No. 08/479,995, filed Jun. 7, 1995 Based on Priority U.S. Appl. No. 06/491,929, filed May 5, 1983.
Perou, C.M., et al., Distinctive Gene Expression Patterns in Human Mammary . . . ,Proc. Natl. Acad. Sci. USA 96:9212-9217 (1999).
Rabbani et al., U.S. Appl. No. 08/574,443, filed Dec. 16, 1995 Abandoned in Favor for U.S. Appl. No. 08/978,632, filed Nov. 25, 1997 and Published as U.S. 2003-0104620.
Rabbani et al., U.S. Appl. No. 09/104,067, filed Jun. 24, 1998 and Subsequently Published as U.S. 2003-0104460 on Jun. 5, 2003.
Robles, J., et al., Towards Nucleopeptides Containing Any Trifunctional . . . Tetrahedron. 55:13251-13264 (1999).
Spellman, et al., Comprehensive Identification of Cell Cycle-Regulated . . . Mol. Biol. Cell 9:3273-3297 (1998).
Stetsenko, D.A., et al., Efficient Conjugation of Peptides to Oligonucleotides . . . J. Org. Chem. 65:4900-4908 (2000).
Taton, T.A. et al., Scanometric DNA Array Detection With Nanoparticle Probes, Science 289:1757-1760 (2000).
Tung, C.H., et al., Preparation and Applications of Peptide . . . Bioconjugate Chemistry 11:605-618 (2000).
Wang, E., et al., High-Fidelity MRNA Amplification for Gene Profiling . . . Nature Biotechnology 18:457-459 (2000).
Weslin, L., et al., Anchored Multiplex Amplification on a Microelectric . . . Biotechnology 18:199-204 (2000).
Yershov, G., et al., DNA Analysis and Diagnostics on Oligonucelotide . . . Proc. Natl. Acad. Sci. USA 93:4913-4918 (1996).
Ying-S-Y., et al., Generation of Full-Length CDNA Library From Single Human . . . ,Biotechniques 27:140-414 (1999).
Borson et al., A Lock-Docking Oligo (DT)Primer for 5' and 3' Race PCR . . . , Methods and Applications (1992) 2:144-148.
Moran et al., Non-Hydrogen Bonding 'Terminator' Nucleosides Increase . . . Nucl. Acid. Res. (1996) 24(11):2044-2052.
Steffens, et al., An Infrared Fluorescent DATP for Labeling DNA, Genome Research (1995) 5:393-399.
Bulyk, et al., Exploring the DNA-Binding Specificities of Zinc Fingers . . . , Proc. Natl. Acad. Sci. USA vol. 98, No. 13, Jun. 19, 2001, 7158-7163.
Morrissey et al., Nucleic Acid Hybridization Assays Employing DA-Tailed Capture Probes . . . , Mol. and Cell. Probes, vol. 3, 1/89, 189-207.
Austermann et al., Biochemical Pharmacology, 1992, vol. 43(12) pp. 2581-2589.
Jones et al.,Changes in Gene Expresssion Associated With Developmental Arrest and Longevity in . . . ,Genome Research, 2001;11:1346-1352.
Gregory et al., Differentially Expressed Abundant Trans-Spliced CDDNAS From Larval Brugia Malayi, Molecular and Biochemical Parasitology 1997;87:85-95.
William Paul, Fundamental Immunology, Second Edition.
Forghani et al., J. Clin. Microbiology, 1991; 29 BOS3:583-591.
Beaudoing, e. et al., Genome Res. 2000;10:1001-1010.
Bouck, J. et al., Nucleic Acids Research, 1998;26:4516-4523.
Schwartz, S. et al., Genes Chromosomes Cancer, 2006;45:770-780.
Niemeyer C.M., et al. Oligonucleotide-directed self-assembly of proteins: Semisynthetic DNA-streptavidin hybrid molecules as connectors for the generation of macroscopic arrays and the construction of supramolecular bioconjugates, Nucleic Acids Res., 1994, 5530-5539, 22.
Armour, "Isolation of human minisatellite loci detected by synthetic tandem repeat probes: direct comparison with cloned Dna fingerprinting probes," *Human Molecular Genetics*, vol. 1, No. 5, pp. 319-323 (1992). 't.
U.S. Appl. No. 08/574,443, filed Dec. 15, 1995, Rabbani et a.
Dietrich et al., "Gene assembly based on blunt-ended double-stranded DNA-modules," *Biotechnology Techniques*, vol. 12 No. 1, pp. 49-54 (1998).
Drygin, "Natural covalent complexes of nucleic acids and proteins: some comments on practice and theory on the path from well-known complexes to new ones," *Nucleic Acid Research*, vol. 26, No. 21, pp. 4791-4796 (1998).
Giller et al., "Incorporation of reporter molecule-labled nucleotides by DNA polymerases. I. Chemical synthesis of various reporter group-labeled 2'deoxyribonucleoside-5'-triphosphates," *Nucleic Acids Research*, vol. 31, No. 10, pp. 2630-2635 (2003).
Nam et al., "Oligo(dT) primer generates a high frequency of truncated cDNAs through internal poly(A) priming during reverse transcription," *Proceedings of the National Academy of Sciences*, vol. 99, No. 9, pp. 6152-6156 (2002).
Niemeyer et al., "Oligonucleotide-directed self-assembly of proteins: semisynthetic Dna—streptavidin hybrid molecules as connectors for the generation of macroscopic arrays and the construction of supramolecular bioconjugates," *Nucleic Acids Res*, vol. 22, No. 25, pp. 5530-5539 (1994).
Petrik et al., "High throughput PCR detection of HCV based on semiautomated multisample RNA capture," *Journal of Virological Methods*, vol. 64, pp. 147-159 (1997).
Stinear et al., "Detection of a single viable Cryptosporidium parvum oocyst in environmental water concentrates by reverse transcription-PCR," *Applied and Environmental Microbiology*, vol. 62, No. 9, pp. 3385-3390 (1996).
Eisen et al., "Cluster analysis and display of genome-wide expression patterns," *Proc. Natl. Acad. Sci.*, vol. 95, pp. 14863-14868 (1998).

\* cited by examiner

Generation of fragmented copies of RNA

RNA

A) Fragmentation of RNA i) Physical fragmentation of RNA ii) Chemical fragmentation of RNA iii) Digestion of RNA with RNaseH after binding of complementary DNA

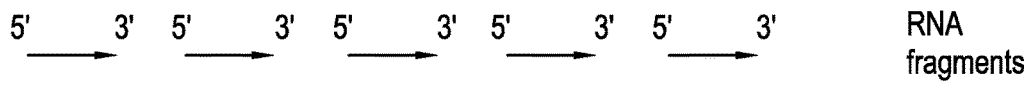
RNA fragments

B) Addition of UDE to fragmented RNA

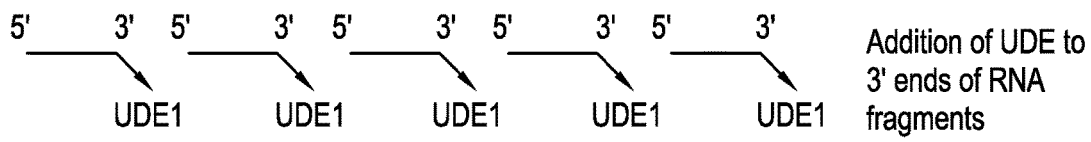
Addition of UDE to 3' ends of RNA fragments

C) Oligonucleotides for transforming RNA into RNaseH substrate i) 3' $N_1N_2N_3N_4N_5N_6N_7N_8$ 5'
(SEQ ID NO: 1)
    Random sequence DNA oligo's ($N_1$-$N_8$) with blocked 3' ends ii) 3' $R_1R_2R_3R_4D_1D_2D_3D_4D_5R_5R_6R_7R_8$ 5'
(SEQ ID NO: 2)
    A DNA segment with a discrete sequence ($D_1$ - $D_5$) flanked by a random ribonucleotide sequence on each side ($R_1$ - $R_4$ and $R_5$ - $R_8$)

iii) 3' $R_1R_2R_3R_4R_5R_6R_7R_8D_1D_2D_3D_4D_5$ 5'
(SEQ ID NO: 3)
    A DNA segment with a discrete sequence ($D_1$ - $D_5$) flanked by a random ribonucleotide sequence on one side ($R_1$ - $R_8$)

iv) 3' $B_1B_2B_3B_4B_5D_1D_2D_3D_4D_5B_6B_7B_8B_9B_{10}$ 5'
(SEQ ID NO: 4)
    A DNA segment with a discrete sequence ($D_1$ - $D_5$) flanked by Universal bases ( B ) on each side

FIG. 1

SEQUENCE LISTING

```
<160> NUMBER OF SEQ ID NOS: 4

<210> SEQ ID NO 1
<211> LENGTH: 8
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(8)
<223> OTHER INFORMATION: a, c, t, g, unknown or other

<400> SEQUENCE: 1 nnnnnnnn                                                                 8

<210> SEQ ID NO 2
<211> LENGTH: 13
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (1)..(4)
<223> OTHER INFORMATION: a, c, u, g, unknown or other
<220> FEATURE:
<221> NAME/KEY: modified_base
<222> LOCATION: (5)..(9)
<223> OTHER INFORMATION: a, c, t, or g
<220> FEATURE:
<221> NAME/KEY: modified_base
<222> LOCATION: (10)..(13)
<223> OTHER INFORMATION: a, c, u, g, unknown or other

<400> SEQUENCE: 2 nnnnnnnnn nnn                                                            13

<210> SEQ ID NO 3
<211> LENGTH: 13
<212> TYPE: DNA
```

```
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (1)..(5)
<223> OTHER INFORMATION: a, c, t, or g
<220> FEATURE:
<221> NAME/KEY: modified_base
<222> LOCATION: (6)..(13)
<223> OTHER INFORMATION: a, c, u, g, unknown or other

<400> SEQUENCE: 3
nnnnnnnnnn nnn                                                            13

<210> SEQ ID NO 4
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(5)
<223> OTHER INFORMATION: Universal base
<220> FEATURE:
<221> NAME/KEY: modified_base
<222> LOCATION: (6)..(10)
<223> OTHER INFORMATION: a, c, t, or g
<220> FEATURE:
<221> NAME/KEY: modified_base
<222> LOCATION: (11)..(15)
<223> OTHER INFORMATION: Universal base

<400> SEQUENCE: 4
nnnnnnnnnn nnnnn                                                          15
```

DUAL POLARITY ANALYSIS OF NUCLEIC ACIDS

CROSS-REFERENCE TO OTHER RELATED APPLICATIONS

This application is a continuation-in-part of application Ser. No. 10/096,076, filed Mar. 12, 2002, which is a continuation-in-part of application Ser. No. 10/693,481, filed Oct. 24, 2003, now abandoned which is a continuation-in-part of application Ser. No. 09/896,897, filed on Jun. 30, 2001, now abandoned the contents of all of which are incorporated herein by reference.

FIELD OF THE INVENTION

This invention relates to the field of nucleic acid detection, including the quantitative determination and characterization of unknown nucleic acids in a sample using an array format.

All patents, patent applications, patent publications, scientific articles and the like, cited or identified in this application are hereby incorporated by reference in their entirety in order to describe more fully the state of the art to which the present invention pertains.

SEQUENCE LISTING

The instant application contains a Sequence Listing which has been submitted electronically in ASCII format and is hereby incorporated by reference in its entirety. Said ASCII copy, created on May 23, 2017, is named ENZ-60-CIP2-SL.txt and is 2,114 bytes in size.

BACKGROUND OF THE INVENTION

The use of arrays to simultaneously quantify a large number of nucleic acid targets in a single experimental sample is an increasingly popular method. There are two areas where this method is most widely used. First is the generation of a mRNA profile to examine effects of different conditions (genetic or environmental) on mRNA expression. Second is the generation of a gene dosage profile to examine the presence of amplifications or deletions of portions of genomic DNA (comparative genome hybridization, CGH).

In the first area, labeled copies (cDNA) have been made from mRNA templates by reverse transcription, or less commonly the mRNA itself has been directly labeled. For examples of the latter, psoralen-biotin (Kumar et al., 2002 Nature Biotechnology 20; 58-63; incorporated by reference herein) and a ligation reaction (Kampa et al., 2002 Genome Research 14; 331-342; incorporated by reference herein) have been used to label purified poly A RNA in studies where there were concerns about avoiding potential artifacts caused by copying reactions.

In the second area involving CGH studies, labeled genomic DNA has been prepared through a nick translation or random primer reaction. An alternative method has been to directly label the genomic DNA itself with chemical reagents. Signals from a test sample can be compared to a standard to indicate the presence of increases or decreases in either genetic representation (CGH) or expression (RNA profiling) of various nucleic acid sequences. The standard can either be done simultaneously or in parallel with the test sample or the standard can even comprise prior or archived data. In many cases, the standard will be a control sample: cells growing under "normal" conditions vs some environmental factor or it can be a transformed cell versus an untransformed cell. In other cases, the standard is of an arbitrary nature, such as in the case, for example, where kidney cell expression is measured and compared to liver cell expression as a reference standard, thereby identifying genes that have differential expression in kidneys versys liver. In another example, lung cancer can be compared to normal lung cells and breast cancer cells and the latter two can serve as reference standards.

In either RNA profiling or CGH array applications, hybridization of the labeled products then takes place with complementary nucleic acids located at various sites on the array followed by quantification of the amount of signal strength at each location. The strands on each site of the array can be single strands comprising synthetic oligonucleotides or polynucleotides that represent a selected portion of the nucleic acid sequence of interest (a monophasic array), or the strands may be derived from denatured double-stranded sources such as bacterial artificial chromosomes (BACs), plasmids or PCR products (biphasic arrays). In the latter case, when labeled mRNA or cDNA were used as probes for mRNA profiling, only one strand has usually served as a target even though both strands are present at each site on the biphasic array.

There are numerous situations, however, where the sample size is insufficient to produce effective amounts of signals on an array and the amount of nucleic acids in the sample needs to be amplified. In the first method that was designed for global amplification of mRNA (and described as the Eberwine process by Van Gelder et al. (1990, Proc. Natl. Acad. Sci. USA 87; 1663-1667, incorporated by reference herein)), a primer with a T7 promoter attached to an oligo-T segment was used to prepare cDNA copies by extension from the poly A region of mRNA to generate a hybrid molecule with the cDNA bound to its complementary mRNA template. In a subsequent step, the method of Gubler and Hoffman (1983 Gene 25; 263-269, incorporated by reference herein) was used to allow portions of the original template mRNA to be used as primers, thereby transforming the original first strand cDNA copies into double-stranded DNA constructs. Because the T7 promoter sequence was included in the original oligo-T primer, the second strand synthesis step converts this primer segment into a functional double stranded-promoter that can be used in a transcription reaction for synthesis of a large number of RNA copies from each DNA template. Unlike the original mRNA which had a poly A segment at the 3' end, the RNA copies made by this amplification method have a poly T sequence at the 5' end, i.e., the RNA copies are the opposite strand of the original mRNA and are sometimes referred to as aRNA. As described previously for labeled cDNA, the labeled aRNA created from the Eberwine process has been used with arrays that have either both strands present (a biphasic array) or have targets with the original mRNA sequences (a monophasic array).

Although this orientation for constructs to make a labeled RNA library is the most common, other methods have been described where a bacteriophage promoter is incorporated into the other end, i.e., the transcription takes place in nucleic acid constructs from the end of the nucleic acid constructs that was derived from the original 5' end of mRNAs, thereby generating sense RNA that is essentially similar to the original starting mRNA. Instead of using the endogenous mRNA templates as a source of primers as described by Eberwine et al., this other method uses an exogenous primer for second strand synthesis. As such, instead of having the promoter in the oligo-T primer, the promoter can now be included in the sequence of the primer for second strand synthesis, thereby reversing the direction of transcription. For examples of various means that have been described for producing a library of sense RNA as an amplified product, see U.S. Patent Application No. 20040161741; Goff et al., 2004 BMC Genomics 5; 76-84; and Marko et al., 2005 BMC Genomics 6; 27-39; the contents of all of which are incorporated by reference.

Labeling of this sense RNA does not produce, however, a product compatible with monophasic arrays that are exclusively designed to hybridize with labeled anti-sense nucleic acids. As such, it was suggested in the aforementioned U.S. Application No. 20040161741 that instead of using monophasic arrays that were complementary to antisense RNA products, the array could be designed for sequences complementary to the original sense mRNA. On the other hand, arrays designed for use with antisense RNA products have been used with amplification processes that generate sense oriented strands by the simple expedient of applying the same solution that was originally used with the unamplified mRNA, i.e., the sense amplification product was used as a template for synthesizing labeled cDNA. It should be pointed out that this reverse transcription step is not necessary when a biphasic array is used that has both strands present at each site or when a small number of commercially available arrays that have oligonucleotide targets from one strand at some locations and targets from the other strand in other locations (Checklt arrays for example, available from Telechem International, Inc. Sunnyvale, Calif., product literature incorporated by reference herein). In these cases, some of the targets on the arrays are compatible with either labeled sense or anti-sense products.

It should also be pointed out that a monophasic array synthesized with oligonucleotides in the anti-sense orientation has recently become commercially available (the Human Exon 1.0 ST Array from Affymetrix, inc. Santa Clara, Calif., product literature incorporated by reference herein). This array was designed by taking exon and EST sequences and using them to design complementary sequences for the array. Kits that have been designed to generate label these are either designed to produce sense strand cDNA products (WT cDNA synthesis and amplification kit, Affymetrix, Santa Clara, Calif.; product literature incorporated by reference) or designed to synthesize both labeled sense and antisense products.

When carrying out RNA profiling studies, the limiting amount of nucleic acids in a sample is not the only concern. First, when carrying out studies on transformed cell lines or tumors, there will often be sufficient material for direct methods of CGH analysis to identify amplifications or deletions of chromosomal content. On the other hand, other specimens may be very small (biopsies or microdissected material) or of low quality (archival biopsy specimens). Second, for the purposes of prognostic diagnosis of cancer, it is often critical to identify chromosomal aberrations prior to there being a significant physical appearance in a tumor. For instance, gross level changes in copy number of the human telomerase gene have been identified in Pap smears by comparative FISH analysis and correlated with predictions of development of cervical carcinoma (Heselmeyer-Haddad et al, 2005 Am J Path 166; 1229-1238, incorporated by reference herein). For the above reasons, numerous methods have been described in the literature for general amplification of chromosomal DNA sequences. For a review of a number of systems used for this purpose see Hughes et al., 2004 Progress in Biophysics and Molecular Biology 88; 173-189, the contents of which are incorporated by reference.

It is easily understood that when doing CGH studies, both strands are present in equal amounts. RNA profiling studies are often carried out, however, on a basic assumption of asymmetry, i.e., when the activity of a particular gene is being studied by means of an oligonucleotide array, it is sufficient to have sequences present from only one strand. What is sometimes if not often overlooked is that transcription is not completely relegated to one strand, even when a single gene is considered. A well-recognized natural phenomenon termed anti-sense regulation takes place in cells where transcription of sequences that are complementary to protein coding mRNA is used by cells to regulate the amount of gene products that are made from the mRNA transcripts. Recent studies that have involved more precise measurement of the extent of sense and anti-sense sequences being transcribed from the same gene have shown that it is possible that more than twenty percent (20%) of transcribed genes have anti-sense counterparts (Chen et al., 2004 Nucl. Acids Res. 32; 4812-4820, incorporated by reference herein).

For studies where both sense and anti-sense poly A mRNA are amplified in an asymmetric manner, the product will still consist of both [+] and [−] strands. For instance, when the Eberwine procedure is used, the mRNA transcript in a sample will generate complementary aRNA strands. In a similar fashion, anti-sense transcripts with polyA ends that may also be present in the sample will likewise be amplified and the complementary strands generated from these templates will comprise sense mRNA sequences. In studies that have used monophasic oligonucleotide arrays for RNA profiling, this duality has been for the most part ignored since only the labeled aRNA amplification products generated signals by hybridizing to the mRNA derived sequences on the array. Expression of anti-sense poly A sequences was not measured in such experiments due to a lack of complementary sequences on the arrays and only changes in mRNA transcription were recognized in these studies. On the other hand, separate assessments for amplified mRNA products and antisense RNA products can be achieved by providing arrays with oligonucleotides that are complementary to each orientation. The foregoing analytical techniques have been used for labeled unamplified RNA samples (Kumar et al., 2002 Nature Biotechnology 20; 58-63; Kampa et al., 2002 Genome Research 14; 331-342, both of which are incorporated by reference).

Even arrays that comprise a single orientation may be confounded by the presence of both sense and antisense sequences in a biological sample when methods of amplification are used that are symmetric in nature. An example of this is the SMART PCR method (Clontech, Mountain View, Calif., product literature incorporated by reference herein), where both mRNA and anti-sense transcripts serve as templates for PCR amplification as long as they have poly A tails. Labeled products made by this process will hybridize to a monophasic array regardless of whether the original template was a sense mRNA or an anti-sense transcript. Under these conditions, this process was not aimed at measuring mRNA transcription levels per se, but rather in measuring the overall gene activity where contributions from both sense and anti-sense transcripts in a sample contribute to the ultimate signal. Similarly, in array systems where both strands are present at each site of the array, signals are generated not only by amplification products of mRNA transcript templates, but also by the amplification products from antisense transcript templates regardless of whether an asymmetric or symmetric amplification process is used. In essence, these arrays also provide a measurement of an overall gene activity without distinguishing whether the signal is derived from copying either sense or anti-sense transcript templates.

When there are broad changes in species that are represented in high numbers in a sample, effects are easily ascertained. Only a certain percentage of the population is, however, sufficiently represented such that the products are capable of generating a detectable signal, i.e., targets that may be present in small numbers cannot be reliably detected above the background levels of the array. The number of targets that can be detected as compared to the number of potential targets is frequently referred to as the "call rate." As one gets closer to background levels, random fluctuations in signal strength become more problematic, even with detectable signals. Furthermore, when a promoter dependent amplification method is used, there are biases involved in having the promoter initiate transcription from sequences that were located at the 3' end or the 5' end of the original mRNA. Thus, when a promoter transcribes from the region originally derived from the 3' end, there is a higher representation of sequences from the 3' region compared to the 5' end in many gene products. The converse also holds true when sequences from the 5' region are used for the start of transcription. Thus there remains a critical need for methods that can increase the reliability of data generated from arrays as well as for methods that can increase the sensitivity of detection of fluctuations in copy numbers of low level target nucleic acids.

SUMMARY OF THE INVENTION

This invention provides a method of characterizing the amounts of nucleic acids in a sample comprising the following three steps. First, there is (i) provided (a) a double-stranded library of linear nucleic acid constructs derived from said sample, wherein each construct comprises (1) a sequence for a first RNA promoter located at one end of the nucleic acid construct, and (2) a sequence for a second RNA promoter located at the other end of the nucleic acid construct; and (b) suitable reactants for carrying out an RNA transcription reaction. In the second step, there are (ii) carried (a) a first transcription reaction with a first portion of the library using the first RNA promoter to generate a first collection of labeled nucleic acid products; and (b) a second transcription reaction with another portion of the library using the second RNA promoter to generate a second collection of labeled nucleic acid products. In the third step, (iii) hybridizing takes place between (a) the first collection to sites on a nucleic acid array, and (b) the second collection to sites on the nucleic acid array or to a different nucleic acid array. In other steps, (iv) measuring the amounts of nucleic acids hybridized to the sites; and (v) comparing the amounts to characterize the nucleic acids in said sample, are carried out.

In another aspect of this invention, a plus-minus determination of nucleic acid quantities in a library can be made. This plus-minus method for determining the amounts of nucleic acids in a library of nucleic acids comprises the following steps. First, there are (i) generated (a) labeled [+] copies of the nucleic acids in the library; and (b) labeled [−] copies of the nucleic acids in the library. Next, (ii) hybridization is effected between the labeled [+] copies and the labeled [−] copies to a nucleic acid array or arrays. Then, (iii) measuring the amounts of hybridization of the labeled [+] copies and the labeled [−] copies to the array is carried out, wherein the amounts of hybridization of the labeled [+] copies and the amounts of hybridization of the labeled [−] copies are independently quantified, thereby determining the amounts of the nucleic acids.

In yet another aspect using different collections of constructs, this invention provides a method of determining the amounts of nucleic acids in a library of nucleic acids. The steps of this method comprise first (i) synthesizing from the library of nucleic acids (a) a first collection of nucleic acid constructs comprising RNA promoters, wherein transcription from the promoters generates [+] copies of the nucleic acids; and (b) a second collection of nucleic acid constructs comprising RNA promoters, wherein transcription from the promoters generates [−] copies of the nucleic acids. Next, there are (ii) generated (a) labeled [+] copies of the nucleic acids from the first collection; and (b) labeled [−] copies of the nucleic acids from the second collection. In the next step, (iii) hybridizing occurs between the labeled [+] copies and the labeled [−] copies to a nucleic acid array or arrays. This is followed by (iv) measuring the amount of hybridization of the labeled [+] copies and the labeled [−] copies to the array or arrays, wherein the amount of hybridization of the labeled [+] copies and the amount of hybridization of the labeled [−] copies are independently quantified, thereby determining the amounts of the nucleic acids.

This invention also provides a method for determining the amounts of DNA and RNA in a library of nucleic acids. In this aspect, the method comprises the steps of (i) generating (a) labeled RNA copies of the nucleic acids in the library; and (b) labeled DNA copies of the nucleic acids in the library; (ii) hybridizing the RNA copies and the DNA copies to a nucleic acid array or arrays; and (iii) measuring the amount of hybridization of the labeled RNA copies and the labeled DNA copies to the array or arrays, wherein the amount of hybridization of the labeled RNA copies and the amount of hybridization of the labeled DNA copies are independently quantified, thereby determining the amounts of the nucleic acids.

This invention is also applicable to the characterization of nucleic acid amounts in a library and a reference library. In this aspect, the method comprises the steps of (i) generating (a) labeled [+] copies of the nucleic acids in the library; and (b) labeled [−] copies of the nucleic acids in said library; (c) labeled [+] copies of nucleic acids in a reference library; and (d) labeled [−] copies of the nucleic acids in the reference library; (ii) hybridizing the labeled [+] copies and the labeled [−] copies to one or more nucleic acid arrays; and (iii) measuring the amounts of hybridization of the labeled [+] copies and the labeled [−] copies to the one or more arrays, wherein the amounts of hybridization of copies (a), (b), (c) and (d) are independently quantified, thereby determining the amounts of the nucleic acids; and (iv) comparing said amounts of the library and the amounts of the reference library, thereby characterizing the amounts of the nucleic acids in said library.

This invention also provides a method of analyzing or characterizing a library of ribonucleic acids. In this method, steps are provided for (i) labeling one portion of the library of ribonucleic acids; (ii) synthesizing cDNA from a second portion of the library of ribonucleic acids; (iii) labeling the cDNA; (iv) hybridizing the labeled library of ribonucleic acids and the labeled cDNA to one or more arrays of oligonucleotides or polynucleotides; (v) quantifying the amount of signal generated from the hybridized labeled library and the hybridized labeled cDNA, wherein the signal generated from the library is distinguished from the signal generated by the cDNA.

The invention also provides a method of comparing expression in at least two samples. In this method, there are carried out the steps of providing labeled [+] copies and labeled [−] copies of nucleic acids in the samples; hybridizing the labeled [+] copies and the labeled [−] copies to one or more arrays, wherein the labeled [+] copies and the labeled [−] copies hybridize to different array sites; and measuring the amount of hybridization on each site of the array or arrays; and comparing the measured amounts.

Another method of characterizing the amounts of nucleic acids in a sample is provided by this invention. In this method, several steps are carried out, including the first step of (i) providing (a) first primers for first strand synthesis and second primers for second strand synthesis, wherein the first primers comprise a first RNA promoter and the second primers comprise a second RNA promoter; (b) suitable reagents for carrying DNA polymerization reactions; and (c) suitable reagents for carrying out RNA transcription reactions. Next, there are carried out (ii) binding the first primers to the nucleic acids in the sample and extending the first primers to form a set of first nucleic acid copies; (iii) binding the second primers to the set of first nucleic acid copies and extending the second primers using the set of first nucleic acid copies as templates, thereby forming a double-stranded library of nucleic acid constructs. Then, there are carried out (iv) (a) a first transcription reaction with a first portion of the library using the first RNA promoter to generate a first collection of labeled nucleic acid products; and (b) a second transcription reaction with another portion of the library using the second RNA promoter to generate a second collection of labeled nucleic acid products. This is followed by (v) hybridizing (a) the first collection to sites on a nucleic acid array, and (b) the second collection to sites on the same nucleic acid array or a different nucleic acid array; and (vi) measuring the amounts of nucleic acids hybridized to the sites; and (vii) comparing the amounts to characterize the nucleic acids in the sample.

Another aspect of this invention concerns a method of characterizing the amounts of nucleic acids in a sample. Several steps are carried out in this method including a first step of (i) providing (a) first primers and third primers for first strand synthesis and second primers and fourth primers for second strand synthesis, wherein the first primers comprise a first RNA promoter and the fourth primers comprise a second RNA promoter; (b) suitable reagents for carrying DNA polymerization reactions; and (c) suitable reagents for carrying out RNA transcription reactions. Next, there is carried out several binding reactions including (ii) binding said first primers to a first portion of the nucleic acids in said sample and extending the first primers to form a first set of first nucleic acid copies; (iii) binding the second primers to the first set of first nucleic acid copies and extending the second primers using the first set of first nucleic acid copies as templates, thereby forming a first double-stranded library of nucleic acid constructs; (iv) binding said third primers to a second portion of the nucleic acids in the sample and extending said third primers to form a second set of first nucleic acid copies; (v) binding said fourth primers to said second set of first nucleic acid copies and extending said fourth primers using the second set of first nucleic acid copies as templates, thereby forming a second double-stranded library of nucleic acid constructs. Then, transcription reactions (vi) are carried out including (vi) (a) a first transcription reaction with said first library using the first RNA promoter to generate a first collection of labeled nucleic acid products; and (b) a second transcription reaction with said second library using the second RNA promoter to generate a second collection of labeled nucleic acid products. The transcription reactions are followed by three steps including (vii) hybridizing (a) said first collection to sites on a nucleic acid array, and (b) said second collection to sites on the same nucleic acid array or a different nucleic acid array; and (viii) measuring the amounts of nucleic acids hybridized to the sites; and (ix) comparing the amounts to characterize the nucleic acids in said sample.

Yet another aspect provided by the present invention is a method of determining the amounts of nucleic acids in a double-stranded library of nucleic acids. Here, the steps comprise (i) generating (a) labeled [+] copies of the first strand of the nucleic acids in said library; and (b) labeled [−] copies of the first strand; (ii) hybridizing the labeled [+] copies and the labeled [−] copies to a nucleic acid array or arrays; and (iii) measuring the amounts of hybridization of the labeled [+] copies and the labeled [−] copies to the array or arrays, wherein the amounts of hybridization of the labeled [+] copies and the amounts of hybridization of the labeled [−] copies are independently quantified, thereby determining the amounts of the nucleic acids.

Another aspect of the present invention is a method of analyzing nucleic acids in a sample. In this method, several steps are carried out including a) providing RNA to be analyzed; b) adding a first sequence to the 3' ends of one portion of the RNA; c) binding a set of first primers to the first added sequence of the first portion, wherein the first primers comprise a first RNA promoter sequence; d) extending the first primers using the first portion of RNA as templates and generating first cDNA copies of the first portion; e) removing the first portion RNA templates; and f) adding a second sequence to the 3' ends of the first cDNA copies of the first portion. Other steps of this method include g) binding a set of second primers to the second added sequence of the first cDNA copies of the first portion; h) extending the second set primer using the first cDNA copies of the first portion as templates, to form double-stranded copies of the first portion; i) adding a third sequence to the 3' ends of a second portion of the RNA; k) binding a set of third primers to the third added sequence in the second portion; l) extending the third primers using the second portion of RNA as templates and generating first cDNA copies of the second portion; m) removing the second portion RNA templates; n) adding a fourth sequence to the 3' ends of the first cDNA copies of the second portion. Other steps follow including o) binding a set of fourth primers to the fourth added sequence of the first cDNA copies of the second portion, wherein the fourth primers comprise a second RNA promoter sequence; p) extending the set of fourth primers using the first cDNA copies of the second portion as templates to form double-stranded copies of the second portion; q) carrying out a transcription reaction with the double-stranded copies of the first portion to generate labeled [−] copies of the RNA; r) carrying out a transcription reaction with the double-stranded copies of the second portion to generate labeled [+] copies of the RNA; and s) hybridizing the labeled [+] copies and the labeled [−] copies to an array or arrays and separately quantifying the amount of hybridization of the labeled [+] copies and the labeled [−] copies.

The present invention also provides a heterophasic array comprising labeled [+] copies of nucleic acids hybridized to the array, and labeled [−] copies of nucleic acids hybridized to the array. In this embodiment, the labeled [+] copies are separately quantifiable from the labeled [−] copies.

BRIEF DESCRIPTION OF THE FIGURES

FIG. 1 illustrates various means of fragmentation of RNA prior to amplification.

DETAILED DESCRIPTION OF THE INVENTION

Definitions

Figure 2:
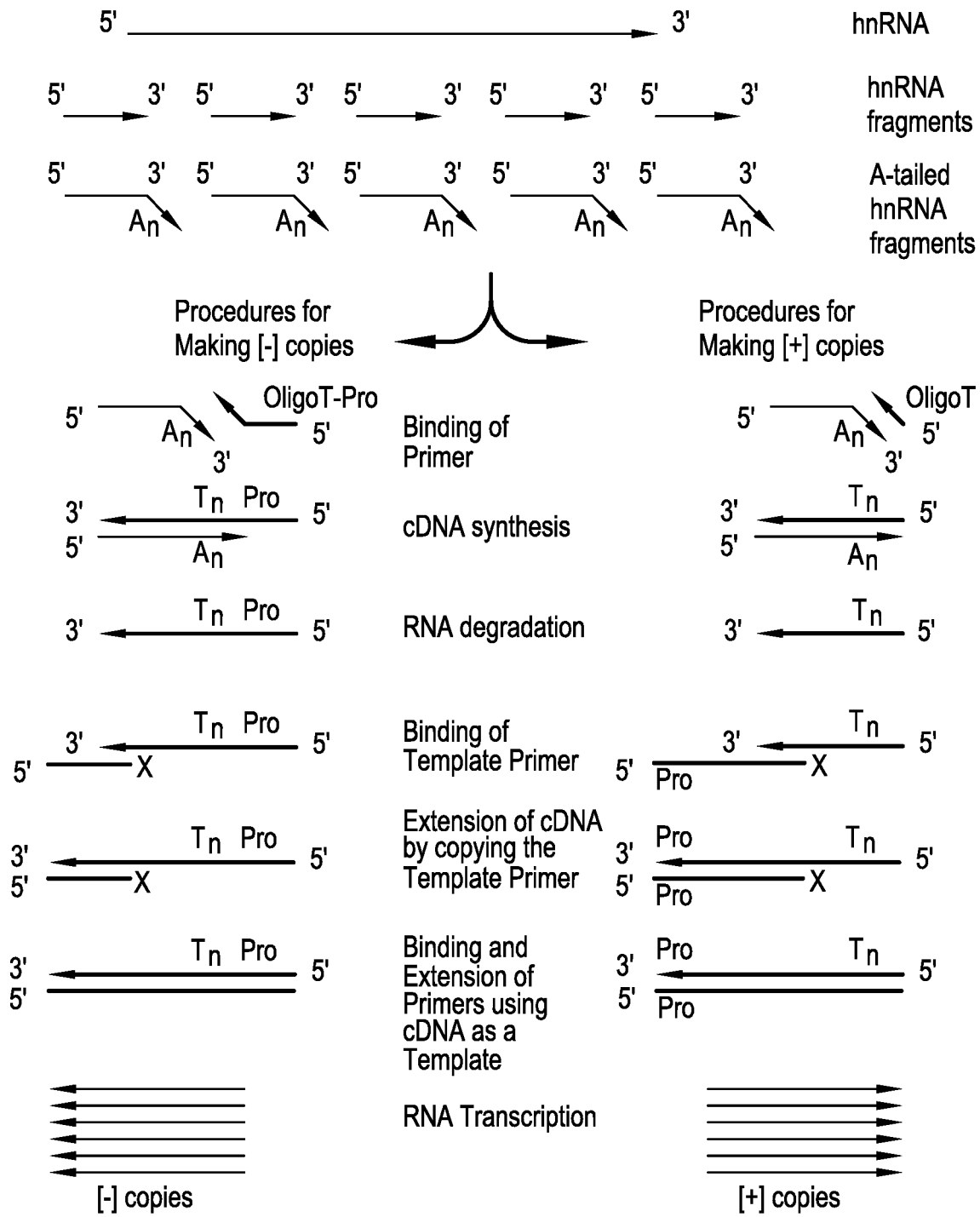
FIG. 2 shows the synthesis of double-stranded constructs for generation of [+] or [−] copies of heteronuclear RNA (hnRNA).

In the context of the present invention, an array is an ordered arrangement of oligonucleotides or polynucleotides fixed or immobilized to a solid matrix, i.e., a non-porous solid support. Microarray is a synonymous term for arrays that emphasizes the size of the space allotted for a particular group of oligonucleotides or polynucleotides on the array. Thus, a microtitre plate and a glass slide with thousands of target spots would both be considered to be arrays. "Bead arrays" (Michael et al., 1998 Anal Chem 70; 1242-1248) where ordering of the particular sequences attached to beads is "decoded" (Gunderson et al., 2004 Genome Research 14; 870-877) are also considered to be covered by the term array or array and are a subject of the present invention.

Targets in the present invention are considered to be nucleic acids that are fixed or immobilized to an array and represent sequences of interest.

A nucleic acid is an oligonucleotide or polynucleotide which may comprise natural nucleotides, modified nucleotides, nucleotide analogues or any combination thereof. A nucleic acid may comprise homopolymeric, low complexity or high complexity sequences. A nucleic acid may be obtained by a chemical or enzymatic method or from a biological source.

The terms "sense" and "anti-sense" strands were originally derived with reference to the "sense" strand of mRNA that coded for a protein and "anti-sense" referred to its complementary sequence. In the present invention, these terms are retained when the present invention is being applied to the analysis of RNA transcripts. However, in addition to mRNA, the present invention also encompasses analysis of transcripts of hnRNA, rRNA, snRNA or any other RNA transcript of interest. Thus polarity is defined with reference to sequences that are identical to transcripts ([+] polarity) and complementary to transcripts ([−] polarity). Thus in the present invention, [+] labeled copies are either the original target strand that has been labeled or a copy has been prepared that comprises identical sequences. Contrariwise, [−] labeled copies are copies that comprise sequences complementary to the original template. The present invention is also applicable to analysis of DNA. Non-limiting examples of techniques where this may be applied included Comparative Genomic Hybridization (CGH) and methylation pattern analysis. In this particular context, the designation of [+] and [−] are of a more arbitrary nature and the terms [+] polarity and [−] polarity emphasize the complementarity of the strands rather than descriptions of functionality inherent in such terms as "sense" and "anti-sense".

A monophasic array is an array where the majority of the targets on the array are represented by a single polarity, i.e either a [+] polarity monophasic array or a [−] polarity monophasic array.

A biphasic array is an array where the majority of the targets on the array are represented by sequences derived from each strand; i.e. both [+] polarity and [−] polarity for the target are at the same site on the array.

A heterophasic array is an array where both [+] and [−] targets are represented for a target of interest, but the [+] and [−] target sequences are at separate spots or locations.

The present invention discloses novel methods and compositions where the identification and quantification of a particular nucleic acid in a sample is represented by hybridization of both a labeled [+] strand copy of the nucleic acid and a labeled [−] strand copy of the nucleic acid to an array. The [+] strand copy may be the original copy of the nucleic acid itself and the [−] sample may a complementary copy that has been synthesized using a similar [+] strand copy as a template. On the other hand, both [+] and [−] copies may be the result of amplification processes that have created numerous copies that comprise sequences that either comprise the same sequence ([+] copies) or a complementary sequence ([−] copies) of the original nucleic acid template. Quantification of [+] copies compared to [−] copies may be carried out simultaneously, sequentially or in parallel.

In the present invention each target sequence in a library can be independently represented by both [+] and [−] copies where the amount of each type of copy is separately determined by hybridization to an array. In some embodiments the present invention, both [+] and [−] copies can be generated by the same construct, for example by a double-stranded DNA molecule with a promoter at each end, where transcription from one promoter provides [+} copies and transcription from the other end provides [−] copies. In other embodiments of the present invention, separate constructs are made where one construct provides [+] copies and the other construct provides [−] copies. With a construct with promoters at each end, a pool can be divided up such that one promoter is used in one set of reactions and the other promoter is used for separate set of reactions. This is especially useful when a different marker is intended to indicate each orientation. On the other hand, it is also possible to carry out transcription simultaneously when each orientation has the same marker and separation of signals is carried out by the identity of the polarity of the target at a given site on the array.

The present invention may be applied to a number of nucleic acids comprising but not limited to RNA from eukaryotic sources such as poly A mRNA or heterologous RNA, RNA from prokaryotic sources, RNA from viral sources, genomic DNA from prokaryotic, eukaryotic or viral sources and artificially synthesized nucleic acids that are a product of one or more nucleic acid copying or amplification reactions.

A large number of RNA profiling studies have had sufficient material that an amplification step was unnecessary. Accordingly, in prior art a common method of producing labeled products for arrays has been the simple step of synthesis of cDNA copies, i.e., the products were in the anti-sense orientation with respect to the original mRNA. Quantification of the original mRNA population was then carried out by measuring the amount of hybridization between the labeled anti-sense cDNA probes and a collection of sense strand targets on a array. As such, each sample gave only one piece of information per target site.

On the other hand, the lack of a sufficient amount of nucleic acids to generate information on levels of specific nucleic acids in some samples has led to the development of a number of different systems for global amplification of nucleic acids. These can be either of a symmetric nature where sequences from each strand are amplified or they can be of an asymmetric nature where one strand of a nucleic acid is preferably amplified.

When using asymmetric means of amplification that employ an RNA promoter, the labeled product has been either the RNA product itself or a labeled cDNA derived from it. In either case, a single orientation of the labeled samples was selected for use with the array. As described previously, since the principle use of this method has been for generation of RNA profiles, the nucleic acid amplification products have been [−] strand copies of the original mRNA that were then hybridized to either biphasic arrays or [+] strand monophasic arrays. With either type of array, a single piece of information has been gained for each nucleic acid sequence being quantified.

With regard to symmetrical means of amplification that have used a PCR type of reaction, even when the initial template comprised sequences from only one strand, the amplification resulted in a library of amplified nucleic acids that comprised sequences from each strand. Similar to the situation with the asymmetric amplification technologies, the labeled products from symmetric amplification have then been hybridized either to a monophasic array that has targets derived from [+] strands or they have been used with biphasic arrays with both [+] and [−] strands at the same target site; in the latter case, the amount of signal contributed from each labeled strand is combined into a single signal for each target site and thus, indistinguishable from each other.

In comparative genomic hybridization (CGH) analysis, both strands are usually labeled and hybridized to an array. However, since the original targets (genomic DNA) comprise both strands in equal amounts and the methods used for either labeling or amplification in CGH should be equal in efficiency for each strand, both strands are usually labeled as probes and both strands are present in the same site on a CGH array, i.e., a biphasic array. Because the signal generated in a CGH assay has been the product of both labeled strands hybridizing to the same site, the particular level of signal strength derived from each strand cannot be distinguished from each other. There has also been an increase in the utilization of oligonucleotide arrays for CGH analysis. (For a recent review, see Yistra et al., 2006 34; 445-450, hereby incorporated by reference). Such arrays have been monophasic arrays, however, where the presence of sequences from only one strand has been deemed necessary and sufficient to quantify genomic targets.

In summary, only a single piece of information has been obtained for a target sequence in prior art. This has been regardless of whether the target was derived from nucleic acids such as DNA that contain both strands or derived from nucleic acids such as poly A RNA that mostly comprises sequences from only one strand. It has also held true for products that have been amplified by asymmetric means such as by an RNA promoter or by symmetric means delivered by a PCR type of amplification.

In contrast to these methods, the present invention discloses novel compositions, methods and assays whose products provide additional information by determining separately and independently the level of hybridization that can take place with hybridization of a library of labeled [+] and [−] copies of a nucleic acid of interest to arrays. It should be pointed out that this is not the same as previous references to measurements of sense and anti-sense poly A transcripts derived from a biological sample. In those studies, the sense and anti-sense transcripts were different nucleic acid species that were independently transcribed from different promoters in vivo. They also were not completely contiguous to each other and would comprise only partial overlaps due to differences in initiation, termination and processing of introns. Again, as was described for other prior art, only a single orientation of the strand was used for measurement for each of the in vivo generated species (sense and antisense RNA). That is to say, measurements of the amount of in vivo sense Poly A RNA was performed by hybridization of the labeled sense mRNA to a [−] monophasic array and measurements of the amount of in vivo antisense RNA was measured by hybridization of the labeled antisense labeled RNA to a [+] monophasic array. As such, a single measurement was generated for each in vivo species. In contrast, the present invention discloses making and separately detecting a [+] and a [−] copy of a sense mRNA with at least one of these orientations being generated in vitro. Furthermore, the present invention also discloses generating and detecting labeled [+] and [−] copies of anti-sense RNA thereby providing two separate measurements for the amount of each initial species of interest.

By carrying out the method of the present invention, two different measurements are independently collected for each nucleic acid sequence of interest, thereby serving as a validation on performance of the system. Thus, when low signals are achieved due to a minority representation within a population, a coincidence of a low signal that is slightly above background from individual measurements of both labeled [+] and [−] strands gives an indication that these are true signals rather than background effects. The present invention may also be employed when analyzing apparent differences in samples where independent assessments of hybridization differences by each strand will allow the user to distinguish between an intrinsic difference in the sample and a difference derived from an experimental artifact. It has been previously noted that the greatest variability in results come from nucleic acid sequences that are present in low numbers and/or exhibit subtle differences in amounts (Nygaard et al., 2005 BMC Genomics 6; 147). Furthermore, when amplification systems are used that are asymmetric in nature, the independent use of each strand as a labeled probe can in principle help diminish strand bias effects, i.e., differential representation of sequences from the 5' and 3' ends.

Any of the various labeling and/or amplification methods that have been previously described in the art for carrying out array analysis of nucleic acids may be used for carrying out the present invention. For instance, labeled nucleic acids used for CGH analysis will usually comprise equal amounts of each labeled strand. These can be hybridized to a heterophasic array where for a given target sequence, there will be a [+] sequence at one location and a complementary [−] sequence at a separate location. If DNA from a test sample is labeled with a first marker and DNA from a control sample is labeled with a second marker, hybridization to the heterophasic array will allow two separate test/control ratios to be generated from the first and second marker readings; i.e. a first/second marker ratio for each [+] loci and a first/second marker ratios for each [−] loci, thereby providing separate assessments of changes in genomic copy levels. In this case 4 data points would be generated for each sequence of interest ([+] and [−] copies of the test sample nucleic acids and [+] and [−] copies of the control sample nucleic acids). In the present invention, any means that are able to label, copy or amplify genomic DNA may find use with the present invention. These can include methods that have been described in the past as well as methods that may be disclosed in the future. The salient point is not with regard to how labeled genomic DNA sequences are generated but the use with such labeled species are made, i.e., information is independently obtained for each strand.

As described previously by others, unamplified mRNA has been used as a template to generate labeled cDNA (a collection of [−] copies) and then hybridized to an array of sense oriented nucleic acids to ascertain an mRNA profile for a sample when there are sufficient amounts of sample available. In addition, we have previously cited examples (Kumar et al., 2002; Kampa et al., 2002) where the mRNA itself was directly labeled and used as a probe (a collection of [+] copies). In contrast to this prior art which is limited to a single orientation, the present invention provides both labeled [+] and [−] copies, thereby doubling the information regardless of whether the information is conveyed by DNA, RNA, or a combination of the two. In addition to the methods that have been described in the references cited previously for directly labeling mRNA, two other non-limiting examples that may be used for this purpose are chemically labeling the mRNA (U.S. Pat. No. 6,262,252 and Hoevel et al., 1999 Biotechniques 27; 1064-1067) or using the poly A region of the mRNA as a Universal Detection Target (UDT) for hybridization of labeled oligo-T as described in U.S. Patent Application No. 20040161741. The contents of the foregoing publications and patent application is hereby incorporated by reference. To carry out the present invention, these labeled libraries could be hybridized to two different monophasic arrays where one monophasic array has [+] orientation nucleic acids and a second monophasic array has [−] orientation nucleic acids. Signals may be separated by carrying out individual hybridizations with each library, i.e. hybridizing the library of [+] copies to a [+]/[−] set of monophasic arrays and the library of [−] copies to a separate set of monophasic arrays. On the other hand, both the [+] library and the [−] library may be hybridized and quantified together if there are different signals associated with each library. A biphasic array, such as those derived from plasmid or PCR products may also be used in this aspect of the present invention. In this case, providing information from whether the signal is derived from the labeled poly A RNA or from the labeled cDNA copy can be carried out either by using separate biphasic arrays for each library or using different labels for each library. As discussed above, the presence of both [+] and [−] strands for each target on a biphasic array implies that the signal from the labeled poly A RNA at each site on a biphasic array will be a compilation of both sense and anti-sense poly A transcripts that were in the original sample and reflects a gene activity measure. Signals from the labeled cDNA copies will also have combined signals derived from the original sense and anti-sense poly A species thereby generating overall gene activity measurements.

Lastly, it should be mentioned that there is a less commonly used type of array (which we have defined as a heterophasic array) that comprises sequences from both sense and antisense strands, but each orientation is fixed to a separate location. In essence, it could be considered to be a combination of putting the features of a [+] monophasic array and a [−] monophasic array onto a single array. The advantage of a heterophasic array is that it is able to serve as a collector for strands in either orientation like a biphasic array, but it has the capability of separating signals for hybridization of each strand rather than co-mingling them as seen with the biphasic array. A commercially available example of this type of array is the Checkit array described earlier. When using a heterophasic array and an experimental sample has the [+] strand copies labeled differently from the [−] strand copies, information of the particular source of the labeled nucleic acid strands hybridized to a each site on the array may be derived from both the difference in signal type, as well as by predetermined information on whether it is a [+] or [−] strand target sequence at that location. Thus, independent data points can be obtained from both [+] and [−] labeled poly A RNA as well as [+] and [−] labeled cDNA copies.

The use of a heterophasic array with the present invention also allows, however, the same label to be used for both [+] and [−] labeled libraries hybridized to the same array where differentiation between signals from the [+] and [−] labeled copies is carried out strictly by the particular location on the array. This method would be of especial use in cases where the heterophasic array has been designed to reduce representation of sequences that are shared by both sense and anti-sense transcripts. Alternatively, it may also be used without such considerations when the particular strand origin is not of importance (i.e., in CGH experiments or assays of overall gene activity) or if in the context of the experiment, the signal contributions from in vivo derived antisense transcripts are considered to be of minimal nature. This method finds utility in the context of experiments where direct comparisons can be made on a heterophasic array with a sample from an experimental condition having a first label and a normal (control) sample having a second label. Thus, a control sample can have both [+] and [−] strand products labeled with a first label and a test sample can have both [+] and [−] strand products labeled with a second label and all four pools can be hybridized simultaneously to a single heterophasic array. Interpretation of the nature of the signal at each site allows independent assessment of each labeled product. It should be pointed out that in the foregoing example, the four pools would comprise a heterogeneous mixture that would include labeled [+] RNA strands as well as labeled [−] cDNA strands being hybridized to an array under a single set of conditions. It is believed, however, that under the conditions normally used for hybridization to arrays, the potential differences between hybridization stability or efficiency for RNA compared to cDNA binding to the array should be of a minimal nature.

Any of the methods that have been previously described in the literature for amplification of the original nucleic acids in samples may also find use with the present invention. When symmetric amplification systems such as PCR are used, the resultant samples can be differentially labeled in each strand by incorporating different labels into each primer. One means for carrying this out has been described in U.S. Patent Application No. 20040161741 (incorporated by reference herein) where Universal Detection Targets (UDT's) are included into the sequences of primers used for amplification. For instance, mRNA can be amplified by synthesizing a collection of cDNAs using an oligo T primer with an arbitrary selected sequence (UDT 1) appended to it. This can then be used as a template by random primers that have a different discrete sequence at their 5' ends (UDT 2) to generate $2^{nd}$ strand copies. Consequently, PCR amplification can then be carried out by using the UDT 1 and UDT 2 sequences as primers where UDT 1 is labeled with Cy 3 and the UDT 2 is labeled with Cy5. The amplified PCR product could then be hybridized to a heterophasic array, a biphasic array or separate monophasic [+] and [−] arrays and each strand of the PCR product individually identified and quantified. Alternatively, the samples may be used with the same label on each strand if they are hybridized to a set of positive and negative monophasic arrays or if they are hybridized to a heterophasic array with each strand located on the same array but in different locations. In this context, labeling can be carried out by incorporating a labeled nucleotide during the amplification reaction. Again, as described previously, when two samples are being compared, a separate label can be used for each sample. Identification of the sample source (sample 1 or sample 2) is carried out by the particular label detected and the source of the strand is carried out by the location of the signal (on the positive or negative array when using monophasic arrays and at the positive or negative location for a heterophasic array).

Asymmetric amplifications such as those that employ phage promoters to carry out RNA transcription based amplification may also find use with the present invention. Thus, as described previously, either [+] or [−] RNA may be generated depending upon whether the promoter is part of the primer used for first strand or second strand synthesis. When one particular orientation is chosen for transcription, this RNA product may be labeled and as described previously, a complementary strand may also be synthesized and labeled while generating cDNA copies. It is also contemplated that dividing pools into reactions that will make either [+] or [−] may be performed. Thus, one amplification reaction can be carried out that involves a promoter being part of the first strand primer and a second separate amplification reaction can be carried out with a promoter being part of the primer used for second strand synthesis. Examples of a number of methods for incorporating a promoter or other desirable nucleic acid sequence into the second strand have been disclosed in U.S. Patent Application No. 20060057583 and U.S. Patent Application No. 20040161741, contents of both incorporated by reference herein. The transcript products for each of these reactions will result in a [−] labeled RNA library and a [+] labeled RNA library, respectively. An advantage of this approach is that it results in a comparison where RNA is compared to RNA as opposed to the example cited earlier which entailed a cDNA vs RNA comparison.

Alternatively, dual promoter constructs may be used where there is a promoter at each end of a construct thereby allowing both [+] and [−] strands to be made from the same construct. This approach will minimize the amount of reagents needed for amplification prior to the transcription reactions and avoid dividing the sample into two separate pools at an early stage. If desired, the promoters in a dual promoter construct may be different from each other so that the same set of constructs can be used to generate a collection of labeled [+] copies in one reaction and a set of labeled [−] copies in another reaction. This would be especially useful when separate labels are desired for each strand product where the nucleic constructs can be divided into two pools where one promoter would use one RNA polymerase to synthesize [+] copies from one end of the constructs and in a separate reaction, a different polymerase is used to synthesize [−] copies from the other end of the constructs. On the other hand, the promoters at each end may be the same promoter when an array is intended to be used that will quantify labeled [+] and [−] nucleic acid copies at different locations (a heterophasic array or separate monophasic arrays) and only a single label may be used for both the [+] and [−] copies. Thus, in this case both [+] and [−] copies can be simultaneously synthesized from a library of nucleic acid constructs in a single reaction. Again as described above, both labeled [+] and [−] products derived from one sample can have one particular label and labeled [+] and [−] products derived from a different sample can have a second label. This approach can be of use, for example, when an experimental sample is being directly compared with a control sample.

Biphasic arrays are more common than heterophasic arrays, but two samples can be compared on the same biphasic array by using a combination of four different labels. Thus, the dividing step that was described above can be used to create a library of nucleic acid from one sample where a first promoter is used to generate labeled [+] copies with label 1 and a second promoter is used to generate labeled [−] copies with label 2. A second sample can then be labeled using the same promoter systems but substituting label 3 and label 4 for the [+] and [−] copies. Thus as long as labels 1, 2, 3 and 4 are distinguishable from each other, a biphasic array can be used to individually quantify each labeled product of two samples on a single array. Separately labeled nucleotides may be used or modified nucleotides with chemically reactive groups may be incorporated, thereby allowing the addition of any desirable label in a post-synthetic reaction. An example of this method is a transcription reaction with allylamine modified UTP followed by addition of an NHS ester of a dye.

One particular consideration in carrying out the method of the present invention is that even when mRNA is being used as a source, it is not completely asymmetric in nature. A fine-detailed mapping of the amount and source of polyA RNA was analyzed by labeling mRNA at the 3' end and hybridizing it to a set of [+] and [−] monophasic arrays that almost completely covered chromosomes 21 and 22 (Kampa et al., 2004, Genome Research 14; 331-342, incorporated by reference herein). This analysis demonstrated that in two cell lines, 11% of the "transfrags" that overlapped known exon, mRNA and EST sequences, were actually in the antisense orientation with regard to these sequences. Also, as previously discussed, some estimates of the number of genes that generate anti-sense as well as sense mRNA have been estimated to be as high as 20%. This indicates that in any preparation of poly A RNA, labeling of anti-sense derived products is always going to be carried out to some degree in addition to mRNA.

As such, when poly A is being analyzed, it may be desirable to have asymmetry artificially added. One way to carry this out is in the design of the arrays, where only sequences are chosen that are known to lack antisense expression. Alternatively, if targets are present in the array that are transcribed as both sense as well as anti-sense and this is a subject of interest, asymmetry can be provided in the labeling reactions where one label will be associated with identical copies of the original target sequences and a second label will be associated with complementary copies of the original target sequences. If one heterophasic array is used for a sample and a second heterophasic array is used for a control, each label on an array can be compared to the other array to independently identify changes in both sense mRNA and anti-sense transcripts.

On the other hand, when symmetric means are being used for amplification, for example RNA samples with the SMART PCR system or DNA samples for CGH studies, both strands are indiscriminately amplified at the same time and an overall assessment of nucleic acid levels is made for each nucleic acid of interest and one marker can be assigned to the test sample and another indicator can be assigned to the control sample. In this case, the signals on an array will represent a summation of signals from both strands in the case of DNA and from both mRNA and antisense RNA in the case of RNA profiling. As described above, an array can be designed such that it detects only the segments of mRNA that have little or no complementary representation of anti-sense RNA. Furthermore, by the use of a system for labeling or amplification that makes use of polyA tails, only anti-sense that also has undergone poly A addition will be generating signals. Lastly, in a method where hnRNA as well as mRNA are quantified, signals are not limited to poly A mRNA and expression in general will be surveyed. In any of the cases cited above, the use of a pair of [+] and [−] monophasic arrays or a heterophasic array can be used to double the information received for each sequence of interest compared to the amount of information achieved previously with a biphasic array or a [+] monophasic array.

It should also be pointed out that the nature of the anti-sense transcription might not always be relevant in methods where both mRNA and anti-sense transcripts become labeled. In the first place, the anti-sense transcripts are not usually complete complementary copies of mRNA; they will usually have their own start and stop signals for transcription. As such an oligonucleotide array can be designed that that comprises only sequences that are absent in anti-sense transcripts. Secondly, for many target sequences the amount of anti-sense RNA transcription may be negligible compared to the amount of mRNA transcription. The studies that were cited previously were not so much concerned about the particular levels of anti-sense so much as discerning whether there was any detectable level of anti-sense transcription for the chromosomal loci being analyzed.

In addition to the previously described arrays that have target specific sequences in specific locations on matrices, there are arrays that use slightly different processes which eventually can generate the equivalent of the more standard monophasic and heterophasic arrays. One example of this type of array is a 'bead array' described in (Michael et al., 1998 Anal Chem 70; 1242-1248, incorporated herein by reference. In this system, there is no pre-ordered arrangement of sequences on a physical matrix. Rather, a collection of separate matrices (beads) is used, where a designated sequence is assigned to each bead. Hybridization of labeled nucleic acids to each bead is followed by randomly sorting out of the beads onto a physical matrix such that each experiment ends up with a unique arrangement of beads making up an array. At this point they are more like a classical array except that the particular sequence is not predetermined as in a normal array but rather there is a decoding step that is used to identify the particular sequence that eventually ended up at each site. (For a fuller description of this last point, refer to "Decoding Randomly ordered DNA Arrays", Gunderson et al., 2004 Genome Research 14; 870-877, incorporated by reference herein). In this particular system, the selection of sequences determines whether the array is equivalent to a standard monophasic or heterophasic array, i.e., for a given nucleic acid of interest, only one strand is represented on the beads (similar to a monophasic array) or contrariwise there may be some beads having sequences from one strand and other beads having sequences derived from the complementary strand (similar to a heterophasic array). It should be pointed out that in the latter case, it would be preferred that when both strands for a given target are used, it would be best that they be derived from different portions of the nucleic acid target sequence to avoid self hybridization between beads. Another solution would be to carry out parallel experiments where one set of beads comprises one orientation and a second set of beads comprises a set of complementary sequences.

Another variant that can be used in the present invention are what are sometimes termed "universal arrays." These are arrays that carry a collection of sequences that are deliberately selected as lacking any complements in the mammalian genome even though their major application is for identification or quantification of mammalian nucleic acid sequences. This seemingly paradoxical choice is dictated by the use of these arrays to provide a single array that can detect labeled nucleic acids having any particular sequences chosen by a user, thereby avoiding the necessity of acquiring custom designed arrays. For a description of arrays that have been used for this method see Gerry et al, 1999 J Mol. Biol. 292; 251-262, Shoemaker et al., 1996 Nature Genetics 14; 450-456, Gharizadeh et al., 2003 Nucl. Acids Res. 31; e146, all of which are incorporated by reference; they are also commercially available as "GenFlex™ TAG arrays" (Affymetrix, Inc. Santa Clara, Calif.) and "Tm100 Universal Arrays" (Tm Biosciences, Toronto, Ontario, Canada). The essential feature of these arrays is that they are used in conjunction with custom designed "adapter' oligonucleotides that have two portions, a first portion comprising sequences that are complementary to one of the sequences that is fixed or immobilized to a particular site on the universal array and a second portion having a sequence that is complementary to a sequence that is of interest to the user.

The adapter molecule can be used for what is some times referred to as SNP (Single Nucleotide Polymorphism) analysis. In one method, the adapter is used as a primer with a polynucleotide of interest as a template, where incorporation or lack of incorporation of a label can be used to indicate the presence of a particular base at the SNP site that is being queried (Fan et al., 2000 Genome research 10; 853-860, incorporated by reference herein) by hybridization of the primer to the universal array to quantify the amount of primers that have acquired a label. They have also been used in ligation based assays where the ligation of the adapter to a labeled second oligonucleotide will be dependent upon the identity of the nucleotide at a SNP site (Gerry et al., 1999 J Mol Bio 292; 251-262, incorporated by reference herein).

Alternatively, the adapter can serve as a bridge between a labeled nucleic acid of interest and the artificial sequence on the universal array. In essence, these universal arrays could act as sandwich hybridization assays that will localize the labeled sequence of interest to a chosen site on the universal array. Examples of commercially available arrays of this type are "GenFlex™ TAG arrays" and "Tm100 Universal Arrays" cited above.

By choosing a set of sequences that are complementary to only one strand of a desirable target, a Universal Array can be transformed into a monophasic array. On the other hand, selection of set of sequences that are derived from each strand of nucleic acid sequence of interest generates can be used to transform a universal array into a heterophasic array.

In another aspect of the present invention, bacterial or heterologous RNA are quantified by the novel methods disclosed above. Additional steps need to be taken for these RNA targets since they are either completely (bacterial mRNA) or mostly (hnRNA) missing poly A tails. With regard to hnRNA, a further consideration is the potentially enormous size of the RNA transcripts. The use of hnRNA could provide a more complete description of transcriptional activity by allowing assessments to be made on introns that are later excised during mRNA maturation as well as RNA species that are non-polyadenylated, a type of RNA that may be involved in control functions.

Due to its large size the use of hnRNA as a target would preferably involve a fragmentation step. This may take place a) prior to making copies of the hnRNA, b) as part of as process for making copies or c) after copies have been made.

Methods for fragmenting hnRNA are well known n the art. For instance, fragmentation of hnRNA can take place by i) physical, ii) chemical or iii) enzymatic means. Examples of mechanical means can include but not be limited to shearing and sonication. Examples of chemical means can include but not be limited to mild alkali treatment with or without metal ions being present. Kits for carrying out this approach are available from a number of commercial sources. Examples of enzymatic means can include but not be limited to nucleases or RNases. Examples of Rnases that may be used for this purpose can include but not be limited to RNase III which uses secondary structure sites as substrates and RNaseH which can digest hnRNA at sites where there is a complementary DNA sequence hybridiszed to the RNA strand. With regard to the latter method the complementary nucleic acids could be random DNA oligonucleotides or they could comprise chimeric oligonucleotides with at least one segment for generating a an RNA/DNA substrate and one or more segments that do not provide a substrate for RNase digestion but do provide stability for binding the chimeric oligonucleotide to the RNA. A description of this method has been previously described in U.S. Patent Application Serial No. 20050137388 (incorporated by reference herein) and is also illustrated in FIG. 1. After fragmentation, a UDE can be attached to the 5' ends, the 3' ends or both 3' and 5' ends of the fragmented RNA to provide promoter sequences, primer binding sites or a combination of the foregoing to carry out amplification reactions. Examples of methods that may be used for carrying out this step can include but not be limited to ligation and extension methods disclosed in U.S. Patent Application Serial No. 20040161741, U.S. Patent Application Serial No. 20060057583 and U.S. Patent Application Serial No. 20050137388, all of which are incorporated by reference.

The fragmented RNA with a UDT incorporated into the 3' ends may be used as a substrate for first strand cDNA synthesis, thereby generating DNA strands with defined sequences at their 5' ends. If desired, unfragmented RNA may also be used as a substrate for cDNA synthesis. Methods that may useful for this purpose can include but not be limited to random priming with the unfragmented RNA as a template or by addition of a UDT to the 3' ends of the unfragmented RNA and using the added sequences as primer binding sites. With regard to the latter method, appendage of a UDT to the 3' end creates a strong bias towards the 3' end sequences and for very large RNA templates, few if any cDNA copies will completely reach the 5' ends. As such, if using unfragmented RNA, it would be preferred to use the random primer method, where the cDNA product should comprise a collection of fragments whose size and 5' end locations depend upon the particular random sites on the RNA template where a primer was bound and extended. This method would also allow the incorporation of UDT's into the 5' ends of the cDNA's by the use of primers that had random 3' ends but had a defined sequence (a UDT) at the 5' end. The UDT in the 5' end could provide a primer binding site, a promoter or a combination of the foregoing in the cDNA products.

Once first strand cDNA has been synthesized from the RNA templates, the series of steps that would subsequently be carried out should be similar to those described for poly A RNA. These can include any of the methods previously described in the literature as well as the previously cited U.S. Patent Application Serial No. 20040161741, U.S. Patent Application Serial No. 20060057583 and U.S. Patent Application Serial No. 20050137388 (all of which are incorporated by reference herein). Examples of methods that may be useful for this purpose may comprise but not be limited to incorporation of a UDT into the 3' ends of $1^{st}$ strand cDNA's by either terminal addition with TDT or the use of a blocked primer with permutational 3' ends. Subsequent amplification steps can be carried out by defined cycle methods such as PCR, multiple synthesis methods such as RNA transcription or combinations of the foregoing. Analysis of the labeled products may be carried out as described above using monophasic, biphasic or heterophasic arrays.

The examples which follow are set forth to illustrate various aspects of the present invention but are not intended in any way to limit its scope as more particularly set forth and defined in the claims that follow thereafter.

DESCRIPTION OF THE PREFERRED EMBODIMENTS

Example 1: Analysis of Biotin Labeled [+] and [−] Copies of Poly A RNA on Monophasic Arrays after Amplification with Single Promoter Constructs a) A set of [+] and [−] monophasic chips can be created by taking the sequences of a commercially available [+] monophasic array and synthesizing oligonucleotides with these sequences as well as their complements as a custom order from a commercial oligonucleotide synthesis vendor. These then can be spotted onto separate arrays using commonly employed procedures to create complementary monophasic arrays (a set of [+] arrays and a set of [−] arrays).

b) Poly A RNA from a biological specimen can be amplified after dividing the sample into two pools. Amplification can then be carried out with each pool by creating first strand cDNAs by priming with an oligo T primer. Synthesis of the complementary second strand cDNAs can then be carried out addition of dCTP to the 3' ends of the first strand products with terminal transferase followed by second strand synthesis with a primer that has a poly G segment as described in U.S. Patent Application No. 20040161741, incorporated by reference herein. For the first pool, the oligo T primer used for first strand synthesis also includes sequences for a T7 RNA promoter. As such, a transcription reaction from the double-stranded construct will generate copies that are complementary to the original poly A RNA sequences. For the second pool, the primer for first strand synthesis would only contain the oligo T sequence but the oligo G primer used for second strand cDNA synthesis would include a T7 RNA promoter sequence. Transcripts from the second pool of constructs will generate nucleic acids that comprise sequences identical to the original mRNA Poly A RNA sequences. For comparison's sake, a similar process can be carried out with a different biological sample that serves as a control sample of poly A RNA. For each of the transcription reactions, biotin-UTP (Enzo Biochem, Inc. NY) can be included as one of the reagents to generate biotinylated RNA products.

c) Hybridization of the pools can be carried out with the monophasic arrays described in step a).

d) The hybridized labeled products could then be detected on the arrays by using phycoerythrin attached to strepavidin (Invitrogen, Carlsbad, Calif.). It should be noted that as described previously, a sample of poly A RNA comprises both sense mRNA that is used for directing synthesis of proteins and anti-sense RNA that may be involved in control of gene expression. In this particular example, both species will be monitored independently by hybridizing each of the pools (with [−] and [+] copies respectively) to individual [+] and [−] monophasic arrays.

For the reactions where the Oligo T/T7 primer was used for first strand synthesis, labeled nucleic acids that are derived from mRNA in the sample (test or control) will be able hybridize to their corresponding sequences on the [+] monophasic array and nucleic acids that are derived from anti-sense RNA transcripts in the specimens will hybridize to their complementary sequences on the [−] monophasic array. This should yield an assessment of the amount of mRNA and anti-sense RNA in the test and control samples, allowing comparisons to be made between the test sample and the control sample for differences in both mRNA and anti-sense RNA levels.

Contrariwise, for the test and control reactions where Oligo T was used for first strand synthesis and the Oligo G/T7 primer was used for second strand synthesis, the labeled nucleic acids derived originally from the mRNA templates will hybridize to the [−] monophasic array and the labeled RNA originally derived from the anti-sense RNA templates will hybridize to the [+] monophasic arrays. This allows an independent assessment of test/control ratios to be made that can be further compared to the ratios derived from the Oligo T/T7 sets of reactions.

Example 2: Analysis of Radioactively Labeled [+] and [−] Copies of Poly A RNA on Biphasic Arrays after Amplification with Single Promoter Constructs A commercially available nylon membrane biphasic array (GF200 Human Gene Filter from Research Genetics, Huntsville Ala.) could be used instead of the custom designed arrays described in Example 1. This type of membrane is a biphasic array where each target locus comprises both strands. In this example, amplification would be carried out as described in Example 1 except that $^{32}P$ labeled nucleotides would be used as the label. After the amplification, the products of each of the four reactions (Oligo T/T7 directed synthesis of [−] copies of the sample, Oligo G/T7 directed synthesis of [+] copies of the sample, Oligo T/T7 directed synthesis of [−] copies of the control, Oligo G/T7 directed synthesis of [+] copies of the control) would be hybridized to an individual nylon membrane and then scanned and quantified using a commercial scanner (STORM PhosphorImager from Molecular Dynamics, Sunnyvale, Calif.). Due to the nature of the biphasic arrays, the amount of signal generated from both mRNA and anti-sense templates will be summed together and serves as a measure of gene activity, i.e., labeled [+] copies of mRNA and polyA antisense from a given genomic segment will generate signals together by hybridizing to each strand on the target sites of one filter and [−] copies of mRNA and poly A antisense from a given genomic site will generate, signals together by hybridizing to each strand on target sites of a separate filter.

Example 3 Analysis of Allylamine Labeled [+] and [−] Copies of Poly A RNA on Heterophasic Arrays after PCR Amplification A custom array would be made as described in Example 1 except that the [+] and [−] strands would be located on the same array although on different sites i.e., a heterophasic array. Theoretically, commercially available arrays with some heterophasic presentation (Check-it Arrays from Telechem International, Sunnyvale, Calif. and 48.5 k Human HEEBO Arrays from Arrays, Inc., Nashville, Tenn.) could be used for this purpose, but each of these chips have only a limited number of targets that are represented by each strand and the particular choice for these targets were for nucleic acids that are stable in terms of representation numbers. Thus, at the present time it would be of more use to custom design heterophasic arrays that specifically comprise sequences that are more likely to exhibit fluctuation levels with variations in genetic and environmental conditions. Such sequences may be chosen as described previously in Example 1.

Amplification could be carried out by using the RNA as a single pool for amplification and an artificial UDT could be included at the 5' end of the Oligo T primer used for first strand synthesis as described in U.S. Patent Application No. 20040161741 and U.S. patent application Ser. No. 10/693,481, contents of both incorporated herein by reference. Although there are a variety of methods disclosed in these patent applications that could be used for this purpose, in this example the enzyme TdT will be used to add a short stretch of dC's to the 3' end of the first cDNA strand. For second strand cDNA synthesis, an oligonucleotide that is blocked at the 3' end and has an oligo G sequence as well as a T7 promoter sequence will be hybridized to the oligo C UDT on the first strand. Although the blocked oligo cannot be extended itself, it can serve as a template for further extension of the first cDNA strand, thereby incorporating the T7 promoter sequence into the 3' end of the first cDNA strand. A series of PCR amplification could then be carried out using a primer with the promoter sequence for one strand and a primer with the UDT sequence as a primer for the other strand. This process could be carried out in parallel with a control sample of RNA for comparison with the results of the test RNA sample.

In the next step, the PCR amplicons from sample and control reactions would be divided into two pools. One pool from the sample PCR reaction would be used for a transcription reaction that includes allylamine UTP to produce labeled RNA. The other pool from the sample PCR reaction would use normal ribonucleotides in a transcription reaction and the unlabeled RNA products would subsequently be used as templates for a revere transcription reaction that includes allylamine dUTP. Thus, both allylamine labeled [+] RNA and allylamine labeled [−] DNA strands will have been generated from the same original sample. This would also hold true for pools made in the same way from the control PCR reaction. By using allylamine in this example, one would minimize differences that may occur due to different affinities for labeled nucleotides by RNA polymerase compared to reverse transcriptase. Post-synthetically, the allylamine labeled products could then be modified by attaching the NHS ester of a Cy3 type dye (Enzo Life Sciences, Farmingdale, N.Y.).

The [+] RNA and [−] DNA from the sample source can be hybridized to one heterophasic array and the [+] RNA and [−] DNA from the control source could be hybridized to a separate heterophasic array. It should be noted that even though both strands are present, the concentrated oligonucleotides on the array should be driving the hybridization and there should be limited hybridization between the RNA and DNA in the liquid phase. This principle is also used in CGH experiments where both labeled strands are always used together. On a further note, unlabeled DNA from the double stranded PCR amplicon should be present in negligible levels compared to the labeled RNA and the labeled cDNA due to the high level of amplification of RNA from each amplicon promoter.

Example 4 Analysis of Digoxygenin Labeled [+] and [−] Copies of Poly A RNA on Heterophasic Arrays after SMART PCR Amplification In this example, the commercially available SMART cDNA synthesis system will be used (Atlas™ SMART™ Fluorescent Probe Amplification Kit, Clontech Laboratories, Mountain View, Calif., product literature incorporated herein by reference) for test samples and control samples of RNA. During the PCR amplification step, digoxygenin dUTP will be included as a label during the amplification step. Thus, both [+] and [−] strands will be labeled simultaneously for each sample.

Hybridization will be carried out with heterophasic arrays similar to the ones described in Example 4 with the sample and control being hybridized to separate arrays, i.e., the test sample product with labeled [+] and [−] strands will be hybridized to one heterophasic array and the control sample product with labeled [+] and [−] strands will be hybridized to a second heterophasic array. Detection of the extent of hybridization could be then carried out by using the Applied Biosystems Chemiluminescence Detection Kit (Applied Biosystems, Foster City, Calif.) and the Typhoon 9410 Imager (GE Healthcare, Piscataway, N.J.).

Example 5 Analysis of Fluorescein Labeled [+] and [−] Copies of Poly A RNA from a Test Sample and Texas Red Labeled [+] and [−] Copies of Poly A RNA from a Control Sample on Heterophasic Arrays after SMART PCR Amplification Amplification can be carried out in parallel for a test sample and a control sample using the SMART PCR system described above. In this example, however, the test sample will be labeled with Fl-dUTP (Enzo Life Sciences, Farmingdale, N.Y.) and the control sample will be labeled with the aphenylic Texas Red (TR)-dUTP described in U.S. Patent Application 20030225247, filed Mar. 12, 2002, the contents of which hereby incorporated by reference. Since the test sample and control sample are now spectrally different from each other, they may be simultaneously hybridized to a single array. In this example, the monophasic arrays described previously in Example 1 will be used. Analysis of the array should generate ratios of test sample compared to control samples. In contrast to the prior art, however, two separate ratio assessments for each nucleic acid of interest can be achieved: Fl and TR labeled [+] strands hybridized to their complementary sequences on the [−] monophasic array to give one ratio and Fl and TR labeled [−] strands hybridized to their complementary sequences on the [+] monophasic array to independently give a second ratio.

Example 6 Analysis of Cy3 Labeled [+] Copies of Poly A RNA from a Test Sample and a Control Sample and Cy 5 Labeled [−] Copies of Poly A RNA from a Test Sample and a Control Sample on Biphasic Arrays after SMART PCR Amplification Dual Label, Using a Transcription Based Modification of the SMART Amplification System and Hybridizing to Biphasic Array A variant of the SMART process is also commercially available that employs transcription as well as PCR amplification (BD SMART™ mRNA Amplification kit, Clontech Laboratories, Mountain View, Calif.). A combination of using transcription as well as PCR for the SMART system has previously been described in the literature by Gustincich et al. 2004, Proc. Nat. Acad. Sci. USA 101; 5069-5074 and Ji et al., 2004 Analyt Biochem 331; 329-339. This method could be adopted for use with the present invention by substituting a primer for poly A tails that includes oligo-T linked to an SP6 promoter for one end and use the SMART primer with a T7 promoter that is included in the kit for the other end. After PCR amplification of a test sample and a control sample by the SMART method, the products can be divided into two separate pools. A first pool for each sample can be used with transcription by T7 in the presence of allylamine-UTP for both the test sample and the control sample to generate allylamine labeled [+] copies. In parallel, a second pool can be used with transcription from the SP6 promoter to generate allylamine labeled [−] copies from the test sample and the control sample. After completion of the reactions, the allylamine labeled nucleic acids can be reacted with appropriate NHS esters to generate fluorescently labeled RNA products. In the case of the T7 generated transcripts, the NHS ester can be Cy3 and the collections of SP6 transcripts can be labeled with Cy5, both dyes being available from GE Healthcare (Piscataway, N.J.). The Cy3 and Cy5 labeled RNA from the control can be mixed together and hybridized to one biphasic array and the Cy3 and Cy5 labeled RNA from the test sample can be mixed together and hybridized to another biphasic array. Detection of Cy3 will allow assessment of the amount of labeled [+] copies binding to their complementary sequences on the biphasic arrays, thus allowing generation of a test/control ratio by comparison of the Cy3 signals from the control and test biphasic arrays at each locus. Detection of Cy5 will also allow, however, assessment of the amount of labeled [−] strands binding to their complementary sequences on the biphasic arrays, thereby allowing generation of a separate test/control ratio. Also, it should be pointed out that due to the design of this particular example, assessments of mRNA and anti-sense transcripts are combined into a single signal and overall gene activity is being measured and compared.

Example 7 Comparative Genomic Hybridization (CGH) Using RNA Transcription Amplification and a Heterophasic Array This particular Example is directed towards detection of amplification of chromosomal DNA segments of chromosome arm 3q, an event that has been associated with tumor development (Heselmeyer-Haddad et al. 2005 Am J. Path. 166; 1229-1238). The initial part of the procedure of this Example has been described by Klein et al. (1999, Proc. Nat. Acad. Sci. USA 96; 4494-4499). Briefly, chromosomal DNA from a sample to be tested for development of cervical carcinoma and a control sample are each digested with Mse I to give fragments ranging from 100 to 1,500 base pairs. T4 DNA ligase is used to add an adapter (UDT) to each end of the fragments that allows a single primer to be used in a subsequent PCR reaction. For this particular example, a variation will be used where the adapter comprises a T7 RNA polymerase promoter segment and linear amplification is carried out rather than PCR as described in Klein et al. (1999). After removing unligated adapters, a transcription reaction can be carried out with allylamine UTP for both the test sample and the control sample. Although, transcription will be taking place concurrently from each end, it has been previously shown that there is surprisingly little interference between the two reactions taking place on the same double stranded fragment and dual T7 promoter vectors are commonly used for generation of high yields of siRNA (Wang et al., 2000 JBC 275; 40174-40179 and Wickstead et al. Mol Biochem Parasit. 125; 211-216). After synthesis, the products could be heat denatured rendering them single-stranded and available for modification in a post transcriptional reaction where the test sample nucleic acids can be modified by the addition of Dylight™ 547 and the control samples with Dylight 647™, active esters of dyes that are available from Pierce Biotechnology, Rockford, Ill.

In this particular example, a defined area of human chromosome arm 3q will be used to design a series of sequences taken from both strands to detect amplification events. The particular sequences for the areas most closely identified with amplification events are located at segments coding for the Human Telomerase Gene (TERC) (Heselmeyer-Haddad et al., 2005 Am J Path 166; 1229-1238). After choosing appropriate sequences, custom arrays can be ordered from Nimblegen, Inc. (Madison, Wis.) for creation of a heterophasic CGH array. Hybridization and detection of the Cy3 and Cy5 nucleic acids can be carried out to determine Cy3/Cy5 ratios for both [+] and [−] strands.

Example 8 Analysis of Labeled [+] and [−] Copies of Poly A RNA from a Test Sample and Labeled [+] and [−] Copies of Poly A RNA from a Control Sample after Amplification with Single Promoter Constructs and Using Heterophasic Arrays and 4 Different Markers The RNA from a test sample and a control sample could each be divided up into separate pools to give a total of 4 pools. As described in Example 1, a T7 promoter sequence can be used as part of a primer for either first strand or second strand cDNA synthesis and the amplification procedure followed basically as described in Example 1. In this example, however, allylamine-UTP will be used as the label for each separate transcription reaction and a different dye will be attached to the allylamine labeled products in the 4 pools to indicate source (test or control) as well as orientation [+] or [−]. A variety of dyes that are spectrally distinct from each other may be used for this purpose. In this example four dyes will be used that have previously been used for sequencing with labeled ddNTP's (Lee et al., 1992 Nucleic Acids Research 20; 2471-2483): 6FAM (520 nm), 5ZOE (540 nm), 5-R6G (555 nm) and NAN2 (585 nm).
In Summary:
Pool A=
Test sample; Oligo-T/T7 promoter primer; 6FAM marker
Pool B=
Test sample; T7 promoter in second strand primer; 5ZOE marker
Pool C=
Control sample; Oligo-T/T7 promoter primer; 5-R6G marker
Pool D=
Control sample; T7 promoter in second strand primer; NAN2 marker
Hybridization can then be carried out simultaneously with all four pools to a single biphasic array. In the same way that four individual dyes can be used in sequencing to indicate the presence of a particular base, each of the dyes now represents a particular sample.

Example 9 Analysis of Labeled [+] and [−] Copies of Poly A RNA from a Test Sample and Labeled [+] and [−] Copies of Poly A RNA from a Control Sample after Amplification with Single Promoter Constructs in Conjunction with Heterophasic Arrays and 4 Different Markers To give wider separation between signals from different labels, a heterophasic chip may also be used with two samples (test and control) that are labeled with four distinct chromophores. In this way, hybridization to the array can result in having only two spectrally distinguishable labels present at each site as opposed to the biphasic array in Example 8, which had four different labels potentially present on each site. By these means, spectral overlap can be minimized as a factor. The amplification and labeling could be carried out as described in Example 8. 6FAM (520 nm) labeled Pool A and 5-R6G (555 nm) labeled Pool C products that were derived from mRNA templates would both hybridize to the [+] sites of the heterophasic array with a peak separation of 35 nm between Pool A and Pool C signals; labeled Pool A and C products that were derived from antisense products would hybridize to the [−] sites of the heterophasic array. Conversely, 5ZOE (540 nm) labeled Pool B and NAN2 (585 nm) labeled Pool D products that were derived from mRNA templates would both hybridize to the [−] strand sites of the heterophasic array with a peak separation of 45 nm between Pool B and D signals; labeled Pool B and D products that were derived from antisense products would hybridize to the [+] sites of the heterophasic array. These results would give two independent assessments of the amounts of mRNA and antisense poly A transcripts present in the test and control samples.

Example 10 Analysis of Labeled [+] and [−] Copies of Poly A RNA from 3 Test Samples and Labeled [+] and [−] Copies of Poly A RNA from a Control Sample after Amplification with Single Promoter Constructs in Conjunction with Heterophasic Arrays and 4 Different Markers RNA samples from a control and three test samples can be amplified individually and used with 4 different dyes to indicate their source. First strand synthesis can be carried out with an oligo T primer to generate cDNA strands from polyA mRNA. After removal of the RNA templates, a ligation can be carried out with the permutational oligonucleotides described in U.S. Patent Application 20060057583. For each sample, a ligation reaction can be carried out with one set of partially double stranded adapter molecules that will add a unique sequence to the ends of 50% of the cDNA strands. After removal of the unligated material, a second set of partially double-stranded adapter molecules can be ligated that will add the unique sequence to the remaining 50% of the cDNA. For the purposes of this example, the unique sequence will be a T7 promoter sequence. The reactions can then be divided up into two pools and labeling carried out essentially as described in Example 3. A first pool will be used in a transcription reaction with allylamine UTP. These will generate copies that are essentially the same sequence as the original nucleic acid strands. For each source a different dye can be attached to the allylamine moieties in the RNA: Alexa Fluor 488, Alexa Fluor 546, Alexa Fluor 594 and Alexa Fluor 647 (Invitrogen, Carlsbad, Calif.). Hybridization to a heterophasic array will allow assessments of the amount of sense and anti-sense present for each sample where the particular fluor will indicate the sample source. The second pool will be used in a transcription reaction with normal nucleotides and then used with reverse transcriptase and allylamine dUTP to generate labeled cDNA copies. Again, the same colored dyes may be used for each sample followed by hybridization to a heterophasic array where quantification of sense and antisense transcripts can be compared with the results obtained with the labeled RNA from the first pool.

Example 11 Bead Array, Single Label

As described earlier, bead arrays are a form of array that may also be used with the present invention. Due to the design of this particular system, the identity of the particular sequence associates with a bead can be arbitrarily assigned a particular code. Thus a sequence derived from one strand (the [+] sequence, for instance) of a target sequence of interest can have one particular code and a sequence from the other strand (the [−] sequence) can have a different code. Thus, functionally speaking, after beads are sorted out to make up an array, it essentially comprises a biphasic array where information on the particular locations of both [+] sequence and [−] sequence beads are decoded after hybridization. In addition for coding for the particular sequence on the bead, however, this system can also be used to assign the particular source of a labeled nucleic acid.

Thus, in the present example, the method of amplification in Example 1 can be carried out where a pool of constructs is made that can be used to generate biotin labeled [+] copies. These can be hybridized to beads with both [+] and [−] versions of the sequences of interest, where the code describes both the identity of the target and its orientation. A second pool made as described in Example 1, can then be used to generate biotin labeled [−] copies. These can be hybridized to a different group of beads, where the coding indicates not only the sequence and orientation, but also that the beads were hybridized to the second pool. This process can be carried out further if the two pools above are made from an experimental sample and they are to be compared to a control. Thus a further step is taken where the control sample is used to make a pool that generates [+] copies (a third pool) and a pool that generates [−] copies (a fourth pool). The third and fourth pools are then hybridized to a third and fourth group of beads respectively, where the coding can be used to indicate sequence, orientation and pool source. After the groups are each hybridized, the beads may be mixed together and sorted out followed by a decoding step. Even though each pool has the same label, the decoding step indicates the particular pool that was used to generate labeled copies as well as the amount from each pool that hybridizes to [+] and [−] beads. Thus both [+] copies and [−] copies are independently used to indicate the amount of mRNA and poly A antisense that was present in the experimental sample and the control sample.

By assigning different decoding numbers for control and sample, they can be distinguished from each other even though the hybridized nucleic acids have the same label. Similarly, with regard to the sequences on the beads, both [+] and [−] sequences for a particular target can be assigned different decoding numbers and again the same label can be used for both the [+] and the [−] strands. Hybridize separately and then distinguish afterwards through decoding whether it was the test hybridization reaction or the control reaction and whether it is the [+] strand on the bead or the [−] sequence on the bead.

Example 12 TAG Array, Single Label

As described previously, a few arrays have been described that are so called "universal arrays" and are commercially available as "GenFlex™ TAG arrays" (Affymetrix, Inc. Santa Clara, Calif.) and "Tm100 Universal Arrays" (Tm Biosciences, Toronto, Ontario, Canada). These are intended to provide universal hybridization to any set of desirable nucleic acid sequences thereby obviating the need to make custom arrays. This particular product essentially uses a variation of sandwich hybridization where adapter oligonucleotides are used that have two segments, a first portion which is complementary to a labeled nucleic acid of interest and a second portion which is complementary to a selected sequence on the TAG array. Hybridization of the adapter to the labeled nucleic acid allows binding of the labeled nucleic acid to a selected site on the TAG array. This method is similar to the bead array above, except that a coding sequence is added that will localize a target sequence to a selected position on the array.

Example 13 Analysis of hnRNA by a Biphasic Array a) Preparation of Biphasic Arrays In this example, amplification and labeling are carried out as described in Example 6, except that sequences are added to the Universal Array to convert it into a biphasic array for selected target sequences of interest.

Biphasic arrays are prepared for an entire chromosome according to the method described in Berton et al., 2004, Science, 306, 2242-2246 where for each target region a sequence is located at one site on the array and its complement is located on a different site.

b) Preparation of Poly A RNA

Complete RNA is isolated from a control sample and an experimental sample using the PureLink Micro-to-Midi Total RNA Purification System (Invitrgogen, Carlsbad, Calif.), and rRNA is removed by the Ribosome Transcriptome Isolation Kit (Invitrogen, Carlsbad, Calif.). The remaining material is fragmented using the Ambion RNA fragmentation kit (Ambion, Inc., Austin, Tex.). Conversion of any 3' Phosphate ends to Hydroxyl ends is carried out by treatment with Calf Intestinal Phosphatase. PolyA Polymerase is then used to add a poly A tail to the 3' termini of the fragments. The tailed material is divided into two pools, Pool A and Pool B which will be used to generate [+] copies and [−] copies respectively.

c) First Strand Synthesis

A library of cDNA copies is made from each of the pools by hybridizing with an Oligo T promoter. In the case of Pool B the first strand primer also has sequences for a T7 Promoter. Extension is carried out by Reverse Transcriptase to generate cDNA copies Pool A will have cDNA strands with oligo T sequences their 5' ends and Pool B will have cDNA strands with oligo T-T7 Promoter sequences at their 5' end.

d) Second Strand Synthesis

RNA templates are removed by treatment with alkali followed by neutralization. Blocked Primers are allowed to hybridize to the 3' ends of the cDNA copies as described in U.S. Patent Application No. 20060057583. For Pool A, the Blocked Primers used in this step will have a T7 promoter sequence followed by a set of N permutational nucleotides. For Pool B, the Blocked Primers will have an Arbitrary Primer Binding Sequence followed by a set of N permutational nucleotides. Since the 3' ends of the cDNAs represent a random set of sequences, the use of the permutational set allows binding events to take place between the Blocked Primers and the 3' ends of the cDNA's followed by extension of the 3' end of the cDNA's thereby incorporating sequences derived from the T7 Promoter (Pool A) or the arbitrary primer binding sequence (Pool B). This is similar to random primer synthesis except that it is the template that undergoes extension instead of the primer. The Blocked Primers are subsequently denatured from their templates and removed from the reaction mixtures. New primers are then added that are capable of extension (i.e., they aren't blocked). In the case of Pool A, these primers comprise the T7 promoter sequence and for Pool B, the complement to the Arbitrary Primer Binding Sequence. Strand extension results in a double set of double-stranded nucleic acid constructs each having a single promoter located at one end. In the case of Pool A, transcription in the presence of allylamine UTP will generate labeled [+] copies of sequences of the original hnRNA and in the case of Pool B, transcription will generate allyamine labeled [-] copies, i.e., sequences complementary to the original sequences of the hnRNA. Because of the number of steps it has taken to reach this point, FIG. 1 presents an illustration of the sequence of the steps described above.

e) Preparation of Fluorescently Labeled Material from Pool A

Post synthetic labeling of Pool A is carried out with Cy3 NHS ester for labeling the experimental sample and Cy5 NHS ester for the control sample.

f) Preparation of Labeled Material from Pool B

Post synthetic labeling of Pool B is carried out with Cy5 NHS ester for labeling the experimental sample and Cy5 NHS ester for the control sample.

g) Hybridization to Biphasic Arrays

Pool A from the experimental and control samples (Cy3 and Cy5 respectively) are hybridized to a biphasic array and Pool B from the experimental and control samples (Cy5 and Cy3 respectively) are hybridized to a separate biphasic array and each spot analyzed for the amount of Cy3 and Cy5 signals and the ratios compared for each array.

Many obvious variations will no doubt be suggested to those of ordinary skill in the art in light of the above detailed description and examples of the present invention. All such variations are fully embraced by the scope and spirit of the invention as more particularly defined in the claims that now follow.

What is claimed is:

1. A method of determining the amounts of RNA transcripts in a sample comprising the steps of:
   (i) generating a library of double-stranded DNA constructs from said RNA transcripts by a process comprising the steps of:
      (a) synthesizing first strand DNA [−] copies of said RNA transcripts; and
      (b) converting said first strand DNA copies into double-stranded DNA copies by synthesizing second strand DNA [+] copies using said first strand DNA copies as templates,
      wherein each double-stranded DNA construct generated comprises a first strand DNA [−] copy of an RNA transcript of the RNA transcripts and a second strand DNA [+] copy of the RNA transcript;
   (ii) preparing
      (a) labeled [+] nucleic acid copies using said first strand DNA [−] copies of the double-stranded DNA constructs as template strands; and
      (b) labeled [−] nucleic acid copies using said second strand DNA [+] copies of the double-stranded DNA constructs as template strands,
      wherein said labeled [+] nucleic acid copies and said labeled [−] nucleic acid copies are complementary to each other, and
      wherein said complementary nucleic acid copies are made using the same double stranded DNA constructs;
   (iii) after step (ii), hybridizing said labeled [+] nucleic acid copies and said labeled [−] nucleic acid copies to a nucleic acid array or arrays; and
   (iv) measuring the amounts of hybridization of said labeled [+] nucleic acid copies and said labeled [−] nucleic acid copies to said array or arrays,
      wherein the amounts of hybridization of said labeled [+] nucleic acid copies and the amounts of hybridization of said labeled [−] nucleic acid copies are independently quantified, thereby determining the amounts of said transcripts,
   wherein,
   (A) said labeled [+] nucleic acid copies and said labeled [−] nucleic acid copies are generated by transcription from a collection of linear nucleic acid constructs derived from said library, wherein a sequence for a first RNA promoter is located at one end of a linear nucleic acid construct and a sequence for a second RNA promoter is located at the other end of said linear nucleic acid construct, wherein said first RNA promoter and said second RNA promoter are different, and wherein said labeled [+] nucleic acid copies are generated by transcribing from said first promoter and said labeled [−] nucleic acid copies are generated by transcribing from said second promoter, or (B) said labeled [+] nucleic acid copies and said labeled [−] nucleic acid copies are generated by transcription from a collection of linear nucleic acid constructs derived from said library, wherein a first portion of said linear nucleic acid constructs comprises a first RNA promoter directing transcription of said [+] nucleic acid copies and wherein a second portion of said linear nucleic acid constructs comprises a second RNA promoter directing transcription of said [−] nucleic acid copies, or (C) said labeled [+] nucleic acid copies and said labeled [−] nucleic acid copies are synthesized from a collection of linear nucleic acid constructs derived from said library, wherein asymmetric PCR is used to amplify one strand of said linear nucleic acid constructs to provide said labeled [+] nucleic acid copies in one reaction and asymmetric PCR is used to amplify the other strand of said linear nucleic acid constructs to provide said labeled [−] nucleic acid copies in a second reaction.

2. The method of claim 1, wherein said labeled [+] nucleic acid copies and said labeled [−] nucleic acid copies are generated by transcription from a collection of linear nucleic acid constructs derived from said library, wherein a sequence for a first RNA promoter is located at one end of a linear nucleic acid construct and a sequence for a second RNA promoter is located at the other end of said linear nucleic acid construct, wherein said first RNA promoter and said second RNA promoter are different, and wherein said labeled [+] nucleic acid copies are generated by transcribing from said first promoter and said labeled [−] nucleic acid copies are generated by transcribing from said second promoter.

3. The method of claim 1, wherein said labeled [+] nucleic acid copies and said labeled [−] nucleic acid copies are generated by transcription from a collection of linear nucleic acid constructs derived from said library, wherein a first portion of said linear nucleic acid constructs comprises a first RNA promoter directing transcription of said [+] nucleic acid copies and wherein a second portion of said linear nucleic acid constructs comprises a second RNA promoter directing transcription of said [−] nucleic acid copies.

4. The method of claim 1, wherein said labeled [+] nucleic acid copies and said labeled [−] nucleic acid copies are synthesized from a collection of linear nucleic acid constructs derived from said library, wherein asymmetric PCR is used to amplify one strand of said linear nucleic acid constructs to provide said labeled [+] nucleic acid copies in one reaction and asymmetric PCR is used to amplify the other strand of said linear nucleic acid constructs to provide said labeled [−] nucleic acid copies in a second reaction.

5. The method of claim 2 or 3, wherein said first RNA promoter and said second RNA promoter are the same promoter.

6. The method of claim 5, wherein said first promoter and said second promoter comprise a T7 RNA promoter, a T3 promoter, or an SP6 promoter.

7. The method of claim 5, wherein said first RNA promoter comprises a T7 RNA promoter sequence, a T3 promoter sequence or an SP6 promoter sequence, and said second RNA promoter comprises a T7 RNA promoter sequence, a T3 promoter sequence or an SP6 promoter sequence.

8. The method of claim 1, wherein said array or arrays is a biphasic array or a heterophasic array.

9. The method of claim 1, wherein said label comprises a fluorescent compound, a phosphorescent compound, a chemiluminescent compound, a chelating compound, an electron dense compound, a magnetic compound, an intercalating compound, an energy transfer compound, or a combination of any of the foregoing.

10. The method of claim 1, wherein said RNA transcripts comprise hnRNA, mRNA, or both.

11. A method of analyzing nucleic acids in a sample comprising the steps of
a) providing RNA to be analyzed, said RNA having been divided into a first portion and a second portion;
b) adding a first sequence to the 3' ends of the first portion of said RNA;
c) binding a set of first primers to said first sequence added to said first portion, wherein said first primers comprise a first RNA promoter sequence;
d) extending said first primers using said first portion of RNA as templates and generating first cDNA copies of said first portion;
e) removing said first portion RNA templates;
f) adding a second sequence to the 3' ends of said first cDNA copies of said first portion generated in step d);
g) binding a set of second primers to said second sequence added to said first cDNA copies of said first portion;
h) extending said set of second primers using said first cDNA copies of said first portion as templates, to form double-stranded copies of said first portion;
i) adding a third sequence to the 3' ends of said second portion of said RNA;
j) binding a set of third primers to said third sequence added to said second portion;
k) extending said third primers using said second portion of RNA as templates and generating first cDNA copies of said second portion;
l) removing said second portion RNA templates;
m) adding a fourth sequence to the 3' ends of said first cDNA copies of said second portion generated in step k);
n) binding a set of fourth primers to said fourth sequence added to said first cDNA copies of said second portion, wherein said fourth primers comprise a second RNA promoter sequence;
o) extending said set of fourth primers using said first cDNA copies of said second portion as templates to form double-stranded copies of said second portion;
p) carrying out a transcription reaction with said double-stranded copies of said first portion made in step h) to generate labeled [−] copies of said RNA;
q) carrying out a transcription reaction with said double-stranded copies of said second portion made in step o) to generate labeled [+] copies of said RNA, wherein said [+] copies and said [−] copies are complementary to each other; and
r) hybridizing said labeled [+] copies and said labeled [−] copies to an array or arrays and separately quantifying the amount of hybridization of said labeled [+] copies and said labeled [−] copies.

12. The method of claim 11, further comprising a step wherein said RNA is fragmented prior to said addition steps.

13. The method of claim 11 or 12, further comprising a step wherein 3' ends that are blocked for extension are unblocked.

14. The method of claim 13, wherein said unblocking step comprises treatment with a kinase, or a phosphatase.

15. The method of claim 12, wherein said fragmentation step is carried out by physical, chemical or enzymatic means.

16. The method of claim 15, wherein said enzymatic means comprise treatment with a nuclease or an RNase.

17. The method of claim 11, wherein one or more of said addition steps comprises a ligation step or a polymerization step.

18. The method of claim 11, wherein said first RNA promoter and said second RNA promoter are the same promoter.

19. The method of claim 18, wherein said RNA promoter comprises a T7 RNA promoter sequence, a T3 promoter sequence or an SP6 promoter sequence.

20. A method of analyzing nucleic acids in a sample comprising the steps of:
 a) providing RNA to be analyzed;
 b) adding a first sequence to the 3' ends of said RNA;
 c) binding a set of first primers to said first added sequence wherein said first primers comprise a first RNA promoter sequence;
 d) extending said first primers using said RNA as templates and generating first cDNA copies of said RNA;
 e) removing said RNA templates;
 f) adding a second sequence to the 3' ends of said first cDNA copies;
 g) binding a set of second primers to said second added sequence wherein said second primers comprise a second RNA promoter sequence;
 h) extending said second set of primers using said first cDNA copies as templates to form double-stranded copies of said RNA;
 i) carrying out a transcription reaction with said double-stranded copies of said RNA to generate labeled [−] copies of said RNA;
 j) carrying out a transcription reaction with said double-stranded copies of said RNA to generate labeled [+] copies of said RNA; and
 k) hybridizing said labeled [+] copies and said labeled [−] copies to an array and separately quantifying the amount of hybridization of said labeled [+] copies and said labeled [−] copies,
 wherein said array is a biphasic array or a heterophasic array.

21. The method of claim 11, wherein the label of said [+] copies and the label of said [−] copies comprise different labels.

22. The method of claim 11, wherein said labeled [+] copies and said labeled [−] copies are hybridized to the same array or arrays.

23. The method of claim 11, wherein said array or arrays comprise a nucleic acid target at one site and a complementary nucleic acid target at a different site.

24. The method of claim 20, wherein the label of said [+] copies and the label of said [−] copies comprise different labels.

25. The method of claim 24, wherein the array is a biphasic array.

26. The method of claim 20, wherein said array is a heterophasic array comprising a nucleic acid target at one site and a nucleic acid complementary to the nucleic acid target at a different site.

27. The method of claim 8, wherein said array or arrays is a heterophasic array.

28. The method of claim 8, wherein said array or arrays is a biphasic array.

* * * * *

UNITED STATES PATENT AND TRADEMARK OFFICE
CERTIFICATE OF CORRECTION

PATENT NO. : 9,777,312 B2  
APPLICATION NO. : 11/444151  
DATED : October 3, 2017  
INVENTOR(S) : Elazar Rabbani and James J. Donegan Page 1 of 1

It is certified that error appears in the above-identified patent and that said Letters Patent is hereby corrected as shown below:

On the Title Page

Under item (63) – the Related U.S. Patent Application Data information should read:
"Continuation-in-part of application No. 10/693,481, filed October 24, 2003, now abandoned, which is a continuation-in-part of application No. 09/896,897, filed June 30, 2001, now abandoned"

Signed and Sealed this
Twenty-sixth Day of December, 2017

Joseph Matal
*Performing the Functions and Duties of the*
*Under Secretary of Commerce for Intellectual Property and*
*Director of the United States Patent and Trademark Office*